United States Patent
Wang et al.

(10) Patent No.: US 10,179,173 B2
(45) Date of Patent: Jan. 15, 2019

(54) SEMI-SOLID DELIVERY SYSTEMS

(71) Applicant: Regents of the University of Minnesota, Minneapolis, MN (US)

(72) Inventors: Chun Wang, Minneapolis, MN (US); Wenshou Wang, Quincy, MA (US); John R. Ohlfest, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 179 days.

(21) Appl. No.: 14/387,178

(22) PCT Filed: Mar. 12, 2013

(86) PCT No.: PCT/US2013/030560
§ 371 (c)(1),
(2) Date: Sep. 22, 2014

(87) PCT Pub. No.: WO2013/142152
PCT Pub. Date: Sep. 26, 2013

(65) Prior Publication Data
US 2015/0283244 A1 Oct. 8, 2015

Related U.S. Application Data

(60) Provisional application No. 61/615,001, filed on Mar. 23, 2012.

(51) Int. Cl.
| | | |
|---|---|---|
| *A61K 47/34* | (2017.01) | |
| *C08G 63/664* | (2006.01) | |
| *A61K 9/51* | (2006.01) | |
| *A61K 9/00* | (2006.01) | |
| *A61K 9/14* | (2006.01) | |
| *A61K 31/192* | (2006.01) | |
| *A61K 31/437* | (2006.01) | |
| *A61K 38/38* | (2006.01) | |
| *A61K 39/00* | (2006.01) | |
| *C08G 65/332* | (2006.01) | |

(52) U.S. Cl.
CPC ............ *A61K 47/34* (2013.01); *A61K 9/0019* (2013.01); *A61K 9/0024* (2013.01); *A61K 9/5153* (2013.01); *A61K 31/192* (2013.01); *A61K 31/437* (2013.01); *A61K 38/385* (2013.01); *A61K 39/0005* (2013.01); *C08G 63/664* (2013.01); *C08G 65/3322* (2013.01)

(58) Field of Classification Search
None
See application file for complete search history.

(56) References Cited

U.S. PATENT DOCUMENTS

| | | | | |
|---|---|---|---|---|
| 4,526,938 A | * | 7/1985 | Churchill | ............. A61K 9/0024 525/154 |
| 5,108,755 A | * | 4/1992 | Daniels | ................... A61L 27/46 424/426 |
| 6,613,355 B2 | * | 9/2003 | Ng | ............................ A61K 8/85 424/424 |
| 6,822,000 B2 | | 11/2004 | Ng et al. | |
| 2003/0130472 A1 | | 7/2003 | Ng et al. | |
| 2003/0138474 A1 | | 7/2003 | Ng et al. | |
| 2003/0212148 A1 | | 11/2003 | Ng et al. | |
| 2006/0155101 A1 | | 7/2006 | Heller et al. | |
| 2009/0011133 A1 | | 1/2009 | Gridnev et al. | |
| 2011/0039794 A1 | | 2/2011 | Corgozinho et al. | |

FOREIGN PATENT DOCUMENTS

WO 2008045425 A1 4/2008

OTHER PUBLICATIONS

Wietor et al.; Macromolecules (2011), 44, pp. 1211-1219.*
Nguyen et al.; Polymer Chemistry (2014); 5, pp. 2997-3008.*
Amsden, et al., "Liquid, injectable, hydrophobic and biodegradable polymers as drug delivery vehicles", Macromol Biosci 10 (8), 825-835 (2010).
Asmus, et al., "Solutions for lipophilic drugs: a biodegradable polymer acting as solvent, matrix, and carrier to solve drug delivery issues", Int J Artif Organs 34 (2), 238-242 (2011).
Einmahl, et al., "A viscous bioerodible poly(ortho ester) as a new biomaterial for intraocular application", J. Biomed Mater Res 50, 566-573 (2000).
Heller, et al., "Development and applications of injectable poly(ortho esters) for pain control and periodontal treatment", Biomaterials 23, 4397-4404 (2002).
Heller, et al., "Poly(ortho esters): synthesis, characterization, properties and uses", Adv Drug Deliv Rev 54 (7), 1015-1039 (2002).
Patent Cooperation Treaty, International Searching Authority, Search Report and Written Opinion for PCT/US2013/30560, 9 pages, dated Jun. 6, 2013.
Schwach-Abdellaoui, et al., "Controlled delivery of metoclopramide using an injectable semi-solid poly(ortho ester) for veterinary application", Int J Pharm 248 (1-2), 31-37 (2002).
Tran, et al., "Controlled release systems containing solid dispersions: strategies and mechanisms", Pharm Res 28 (10), 2353-2378 (2011).
Uhrich, et al., "Polymeric systems for controlled drug release", Chem Rev 99 (11), 3181-3198 (1999).
Zhao, et al., "Molecular Nanoworm with PCL Core and PEO Shell as a Non-spherical Carrier for Drug Delivery", Macromolecular Rapid Communications 33, 1351-1355 (2012).

* cited by examiner

*Primary Examiner* — Jeffrey T. Palenik

(74) *Attorney, Agent, or Firm* — Viksnins Harris Padys Malen LLP

(57) ABSTRACT

The invention provides semi-solid systems for delivering biologically active materials that include a polymer comprising 1) one or more units of formula Ia, IIa, or IIIa: (formula Ia, IIa, IIIa) and 2) one or more units comprising polycaprolactone; wherein R and $R_a$ have any of the values defined in the application.

17 Claims, 24 Drawing Sheets

(A) Precursor of monomer 1

(B) Monomer 1

(C) Precursor of monomer 2

(D) Monomer 2

(E) PCL-OE-1

(F) PCL-OE-2

SEMI-SOLID DELIVERY SYSTEMS

PRIORITY OF INVENTION

This application is a 371 of PCT/US2013/030560 filed on 12 Mar. 2013 which claims priority from United States Provisional Application No. 61/615,001 filed on 23 Mar. 2012. The entire contents of the foregoing are incorporated herein by reference.

STATEMENT OF GOVERNMENT RIGHTS

This invention was made with government support under R01CA129189 awarded by the National Institutes of Health. The government has certain rights in the invention.

BACKGROUND OF THE INVENTION

Because of their excellent biocompatibility and adjustable degradation rate, biodegradable and biocompatible polymers have been extensively studied as drug controlled release carriers. Besides selecting the optimal polymer for specific drug delivery purpose, how to incorporate drugs efficiently into polymers is another important issue. Polymers have been prepared into different physical forms, such as micelles, nanoparticles, microspheres, films, gels, to facilitate the encapsulation and controlled release of drugs (see Uhrich, K. E., et al., Chem. Rev. 1999, 99, 3181-3198). In spite of all the advances made, there is much to be further improved. First, most micelles, microspheres or particles often have low drug loading efficiency, as low as a few percent in some cases. Second, many formulation technologies need the assistance of organic solvents to dissolve drugs during dosage preparation and processing. However, the use of organic solvents might be detrimental to delicate drugs such as proteins or peptides, and the residual solvent could be a safety concern for human use. The emergence of injectable biodegradable polymers holds promise in solving these problems (see Amsden, B. Macrom. Biosci. 2010, 10, 825-835; and Heller, J, et al., Adv. Drug Deliv. Rev. 2002, 54, 1015-1039). Drugs could be mixed with or dissolved in viscous semi-solid polymers directly at room temperature with loading efficiency of 100%, and the facile incorporation is especially beneficial for those thermally sensitive or solvent-sensitive drugs such as proteins and peptides. The injectability of semi-solid polymers and administration via minimally invasive means is another advantage.

Currently there remains is a large unmet need for better delivery systems to achieve sustained release of drugs and other biologically active agents at prescribed durations.

SUMMARY OF THE INVENTION

A new semi-solid polymer based material has been identified that is a semi-solid material at room and physiological temperatures allowing easy formulation of drugs (e.g. by simple mixing) and delivery by minimally invasive injection or topical application (to the skin). The material is capable of loading and releasing a wide range of drugs either hydrophobic or hydrophilic, including small molecule drugs, and macromolecular drugs such as proteins, peptides, polysaccharides, nucleic acids. For example, the polymers can be used to deliver tumor antigens and immunostimulatory adjuvants. Additionally, the polymer chemistry utilized for the preparation of the semi-solid polymers allows for easy tuning of drug release rate to suit different application requirement. The materials have the additional advantages of being synthesized easily from biocompatible building blocks, so that the degradation products are biocompatible. The materials also offer the advantage of being synthesized using commonly available molecules, so that their preparation is cost-effective.

Accordingly, in one embodiment the invention provides a polymer of the invention which is a polymer comprising 1) one or more units of formula Ia, IIa, or IIIa:

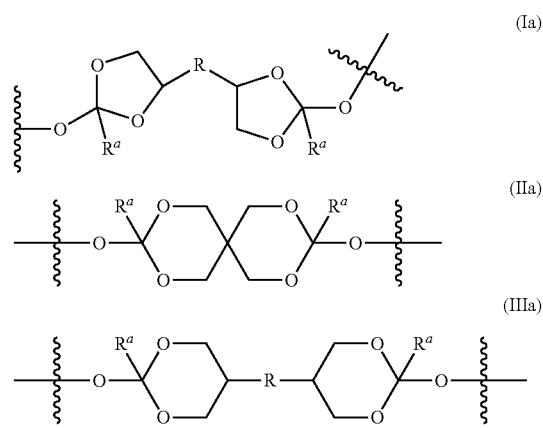

and 2) one or more units comprising polycaprolactone; wherein:

each R is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl; and each $R_a$ is independently hydrogen, $((C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, or $(C_1-C_{10})$alkyl-O—$(C_1-C_{10})$alkyl.

The invention also provides a pharmaceutical composition comprising a polymer of the invention and a biologically active agent.

The polymers of the invention can be used as a controlled release system for a very broad range of cargos including small molecular drugs, large molecular drugs such as proteins (including antibodies), peptides, polysaccharides, nucleic acids, or multiple cargos of these kinds combined in a single system. The material is a semi-solid so it is most suited for parenteral delivery of drugs through injection or topical application to the skin. Applications include drug delivery in disease treatments that require parenteral delivery, such as cancer therapy, anti-inflammatory anti-infectious therapies, neurological drug therapy including pain relieve, vaccine formulation and adjuvant delivery, and drug therapies to treat skin disorders and metabolic diseases such as diabetes.

The invention also provides processes and intermediates disclosed herein that are useful for preparing the polymers of the invention.

DETAILED DESCRIPTION

Figure 1:
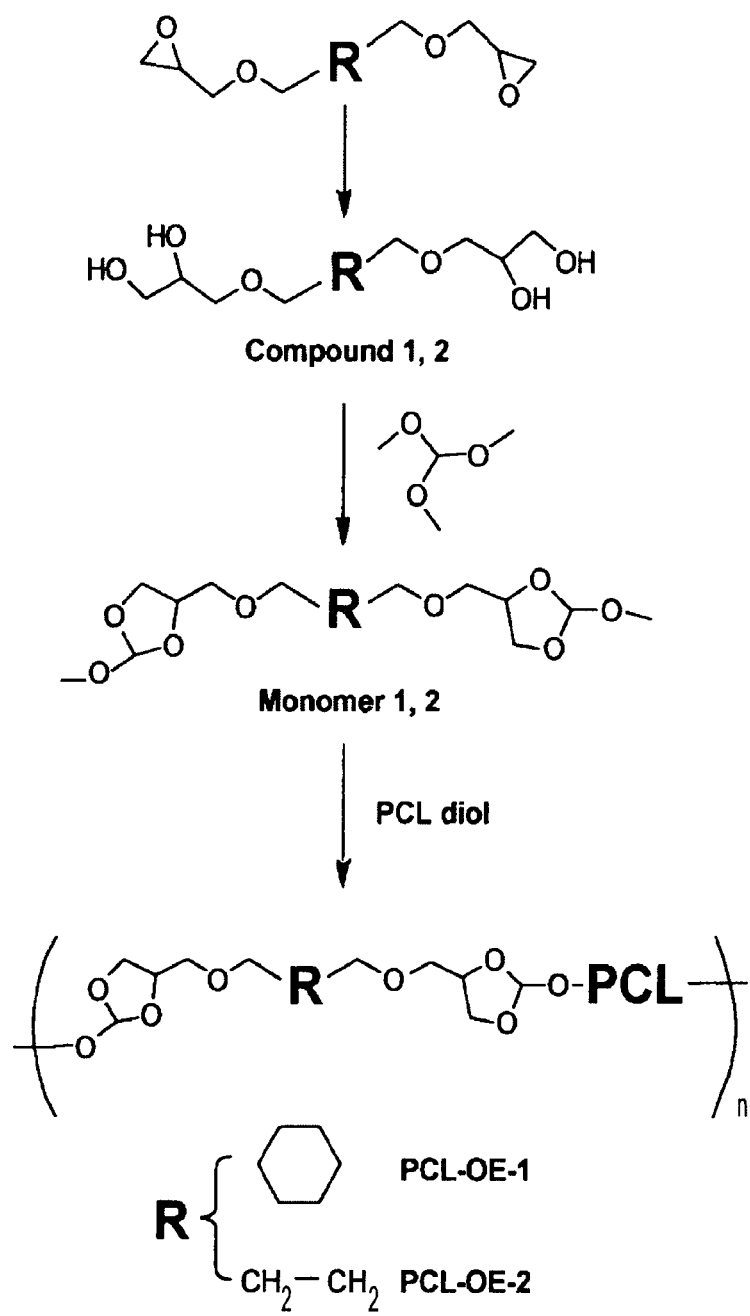
FIG. 1. Illustrates the synthesis of a representative polymer of the invention.

The following definitions are used, unless otherwise described: halo is fluoro, chloro, bromo, or iodo. Alkyl denotes both straight and branched groups; but reference to an individual radical such as propyl embraces only the straight chain radical, a branched chain isomer such as isopropyl being specifically referred to. Aryl denotes a phenyl radical or an ortho-fused bicyclic carbocyclic radical having about nine to ten ring atoms in which at least one ring is aromatic.

The abbreviations POE-CL (polyorthoester-caprolactone) and PCL-OE (polycaprolactone-orthoester) may be used interchangeably herein and in U.S. Provisional Application No. 61/615,001.

Specific values listed below for radicals, substituents, and ranges, are for illustration only; they do not exclude other defined values or other values within defined ranges for the radicals and substituents Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl, or decyl; and $(C_3-C_8)$cycloalkyl can be cyclopropyl, cyclobutyl, cyclopentyl, cyclohexyl, cycloheptyl, or cyclooctyl.

The polymers of the invention can be formulated as pharmaceutical compositions and administered to a mammalian host, such as a human patient in a variety of forms adapted to the chosen route of administration, e.g., topical or injection.

The polymers can be administered by injection in pure liquid form, or as solutions, or as dispersions. Solutions of the polymers can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions can be prepared by incorporating the polymers in the required amount, either in pure liquid form, or in the appropriate solvent with other ingredients enumerated above, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compositions may be applied in pure form. However, they may also be administered to the skin as compositions or formulations, in combination with a dermatologically acceptable carrier.

Useful dosages of the biologically active agents can be determined by comparing their in vitro activity, and in vivo activity in animal models. Methods for the extrapolation of effective dosages in mice, and other animals, to humans are known to the art; for example, see U.S. Pat. No. 4,938,949.

The amount of the biologically active agent required for use in treatment will vary not only with the particular biologically active agent selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Polymers of the Invention

Figure 2:
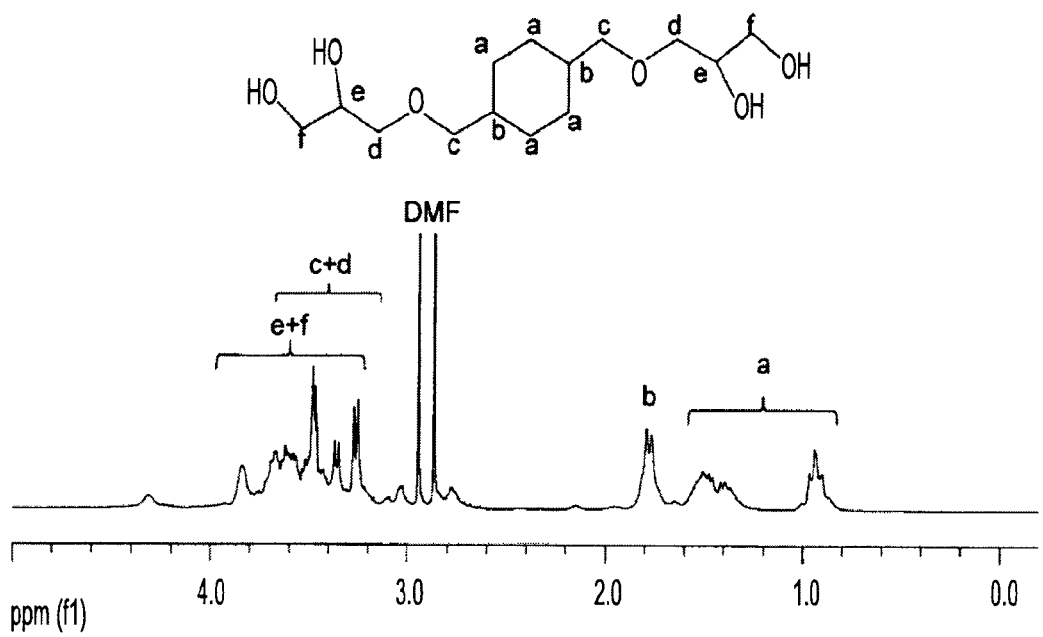
FIG. 2. Illustrates proton NMR data for the compounds and polymers synthesized in Example 1.
Figure 2:
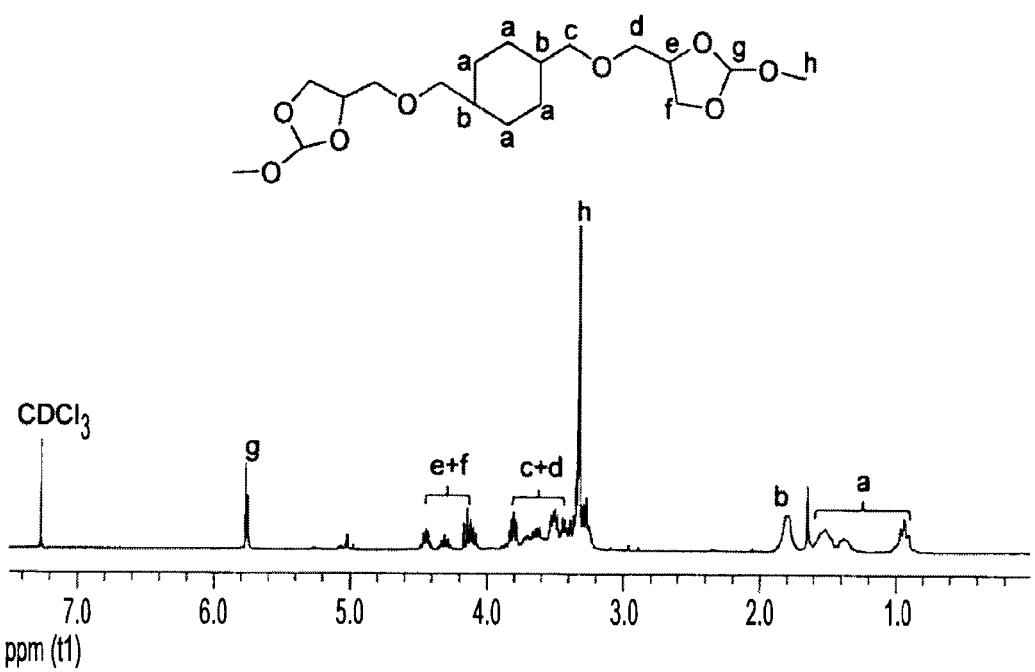
Figure 2:
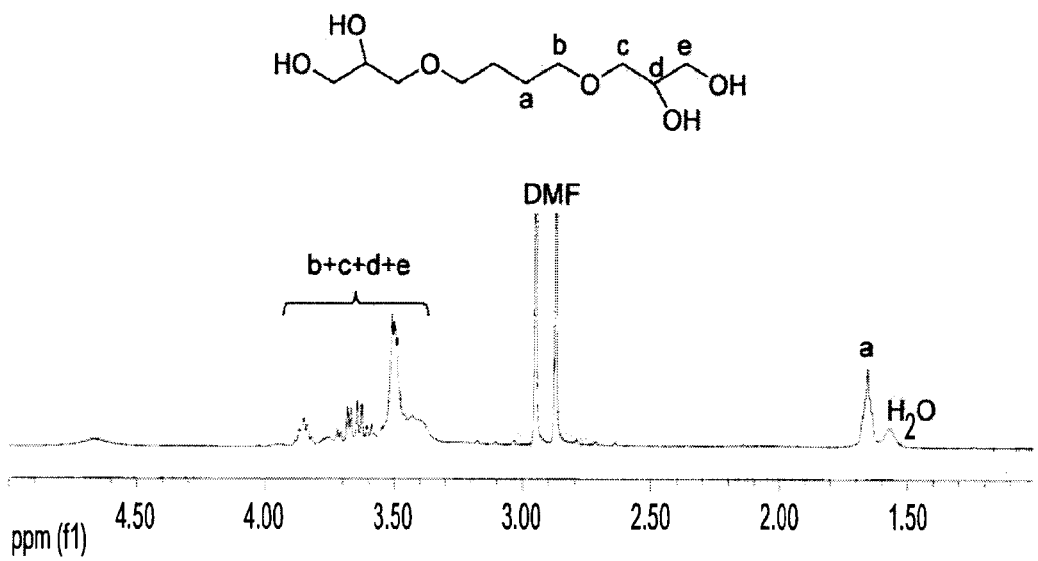
Figure 2:
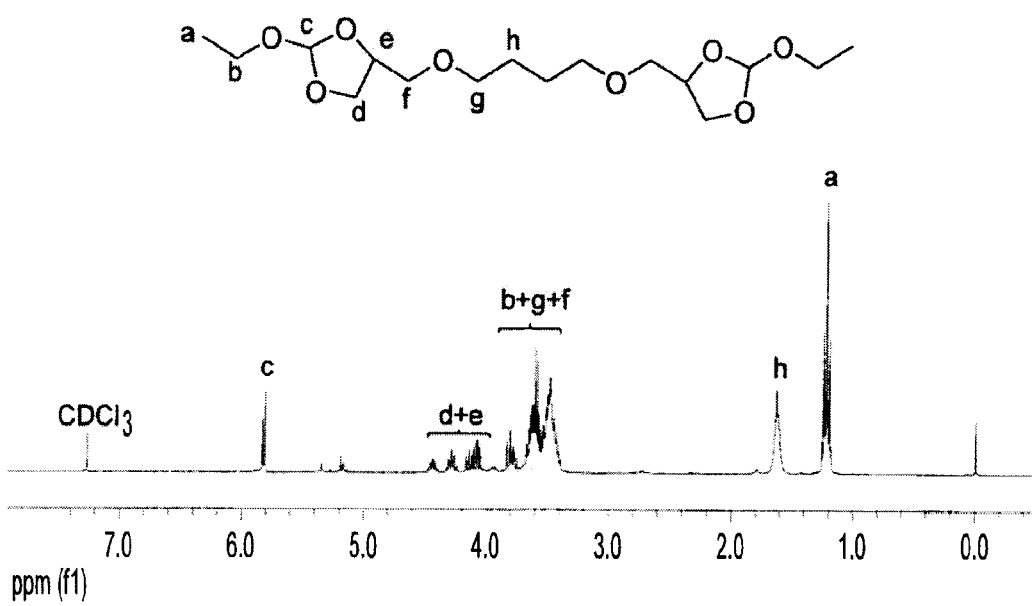
Figure 2:
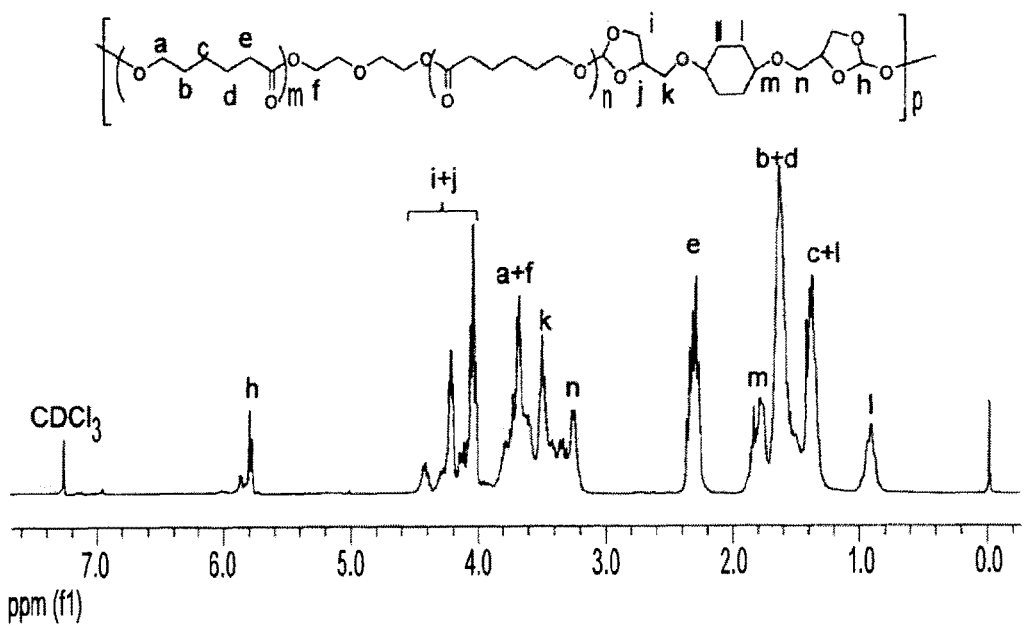
Figure 2:
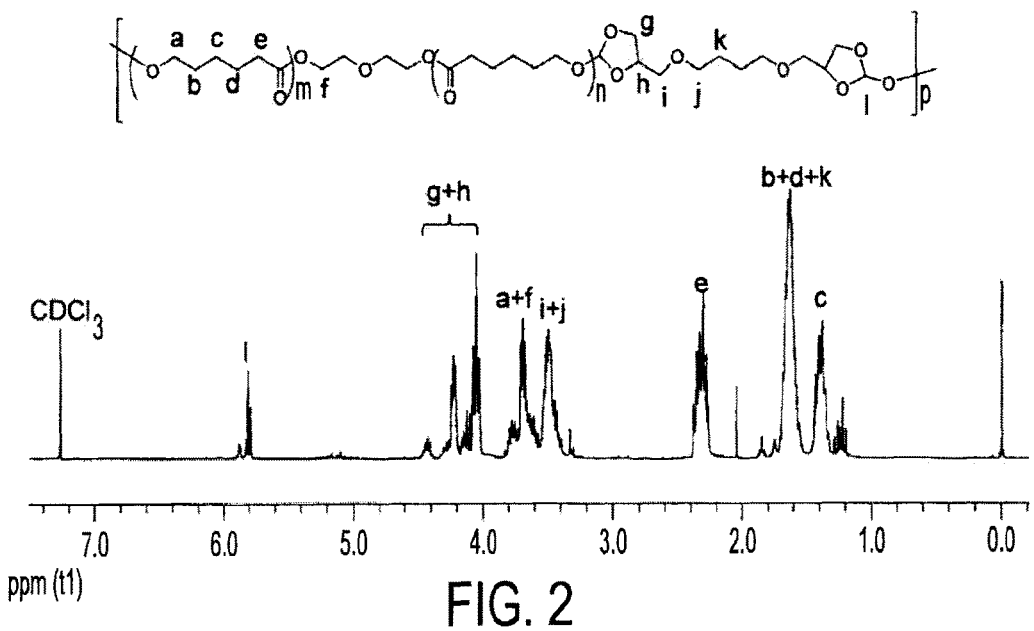
Figure 3:
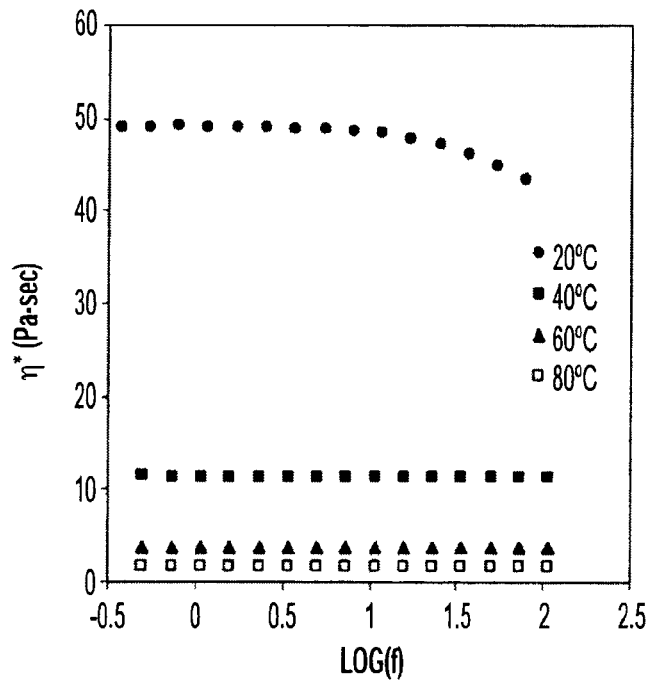
FIG. 3. Illustrates Rheological studies and injectability of the semi-solid polymers. (A) Frequency sweep of PCL-OE-1 at various temperature; (B) Frequency sweep of PCL-OE-2 at various temperature; and (C) Compound viscosity and temperature dependence of viscosity are dependent on polymer composition (shear frequency was 1 Hz). Compound viscosity of the polymers was measured at different temperature and shear frequency. As temperature increased, polymer viscosity decreased sharply. At constant temperature, the polymer maintained constant viscosity without substantial thinning or thickening. Viscosity of the polymers was dependent on the polymer composition. Both polymers were injectable at room or physiological temperature through a needle.
Figure 3:
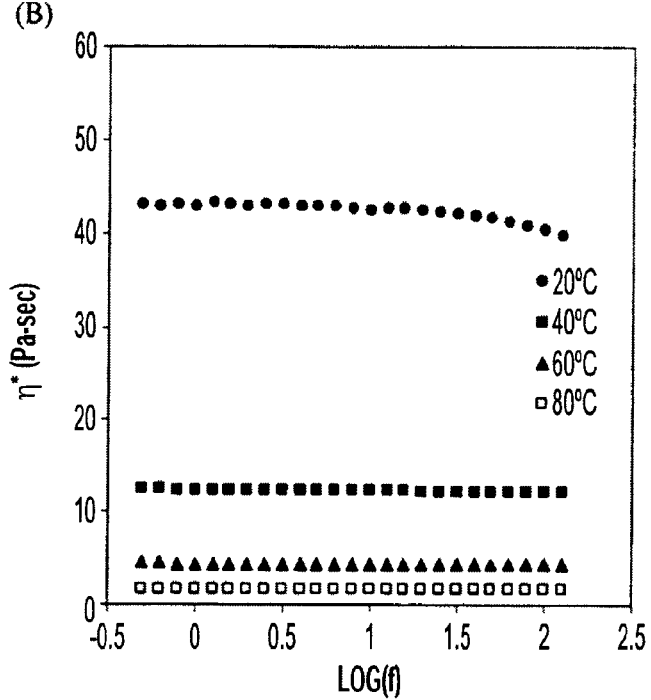
Figure 3:
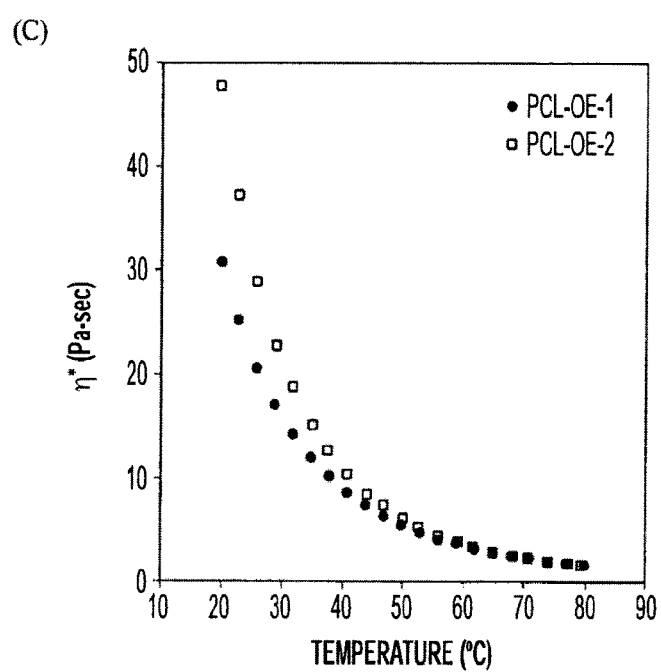
Figure 4:
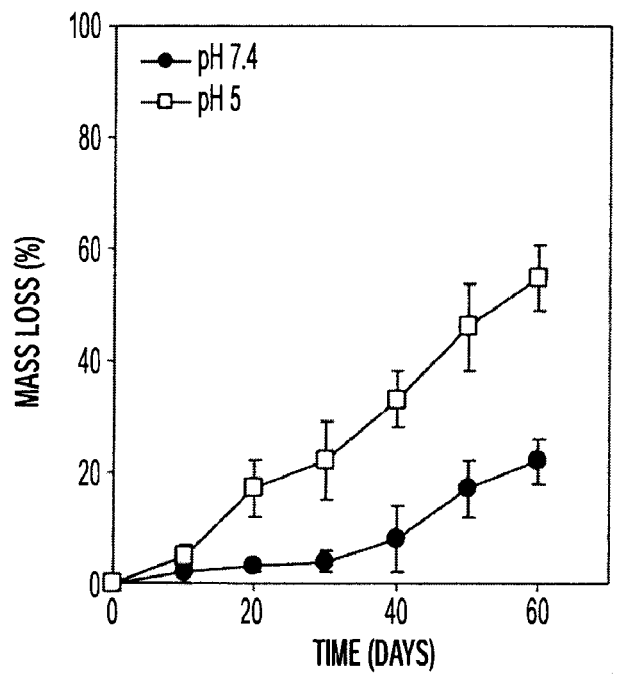
FIG. 4. Illustrates hydrolysis data of the semi-solid polymers measured by the loss of polymer mass over time in aqueous buffer of different pH. (A) PCL-OE-1; (B) PCL-OE-2. For both polymers there was an acceleration of polymer erosion at mildly acidic pH 5.0 than pH 7.4, which demonstrates the control of polymer degradation through hydrolysis of the ortho ester bond in the polymer backbone, which was verified by the disappearance of the characteristic proton NMR peak at 5.8 ppm. Furthermore, polymer degradation rate was dependent on polymer composition. PCL-OE-2 degraded faster than PCL-OE-1.
Figure 4:
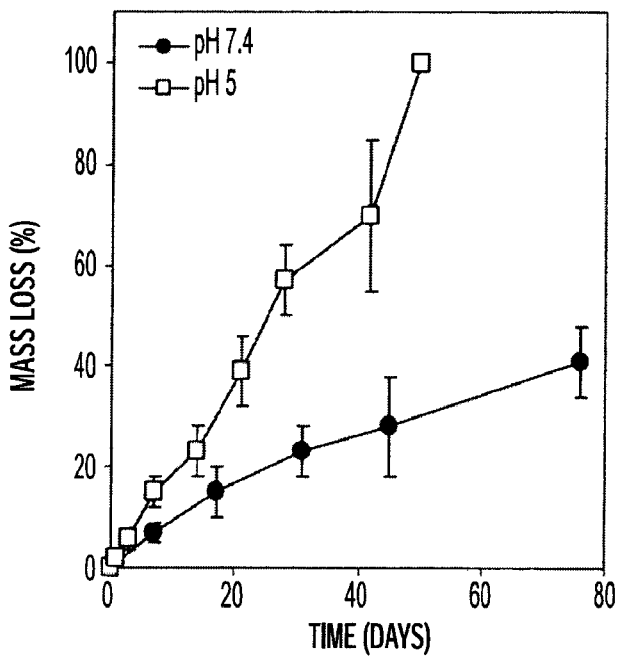
Figure 5:
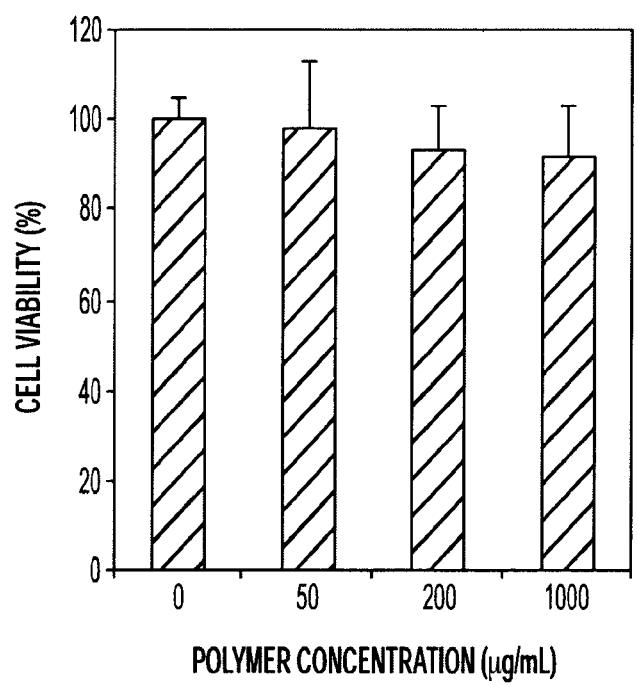
FIG. 5. Illustrates toxicity data in fibroblast cells in vitro after incubating cells with semi-solid polymer for 24 hours. There was no toxicity, even with polymer concentration as high as 1 mg/mL.
Figure 6:
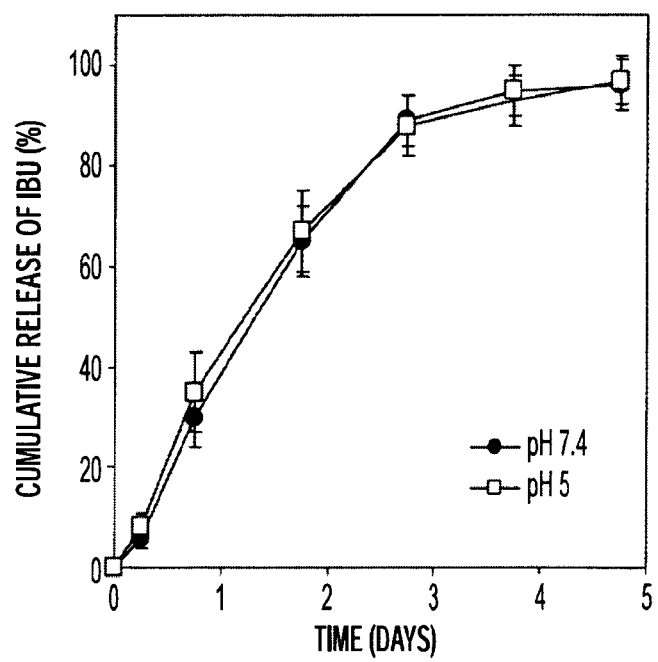
FIG. 6. Illustrates release kinetics of a small molecule hydrophobic drug (Ibu) and a hydrophilic model protein drug (BSA) in aqueous media at physiological pH 7.4 and mildly acidic pH 5.0. (A) Release kinetics in vitro of Ibu from the semi-solid polymer. The sustained release of Ibu was achieved to last for at least three days. Because the polymer itself has not degraded substantially during this time frame, the sustained release of Ibu is not affected by pH and is controlled by diffusion through the hydrophobic semi-solid polymer matrix; (B) Release kinetics in vitro of BSA from the semi-solid polymer. The release of BSA at pH 7.4 started with a fast burst phase followed by a sustained phase through three weeks at which point more than 50% of the protein has been released. Selecting a more hydrophilic semi-solid polymer composition should extend the release beyond this point. At mildly acidic pH 5.0 the release of BSA was much accelerated and the release was sustained to completion by week 4. This example highlights the important utility of the semi-solid polymer for sustained release of drugs in normal human body tissue with physiological pH and in acidic human body tissue environment (such as site of inflammation, chronic wound, bone resorption, microbial infection, and solid tumors).
Figure 6:
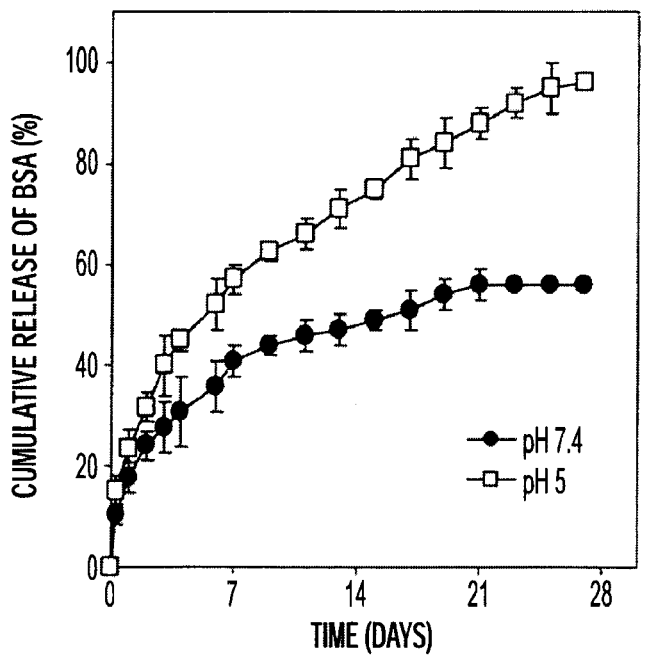
Figure 7:
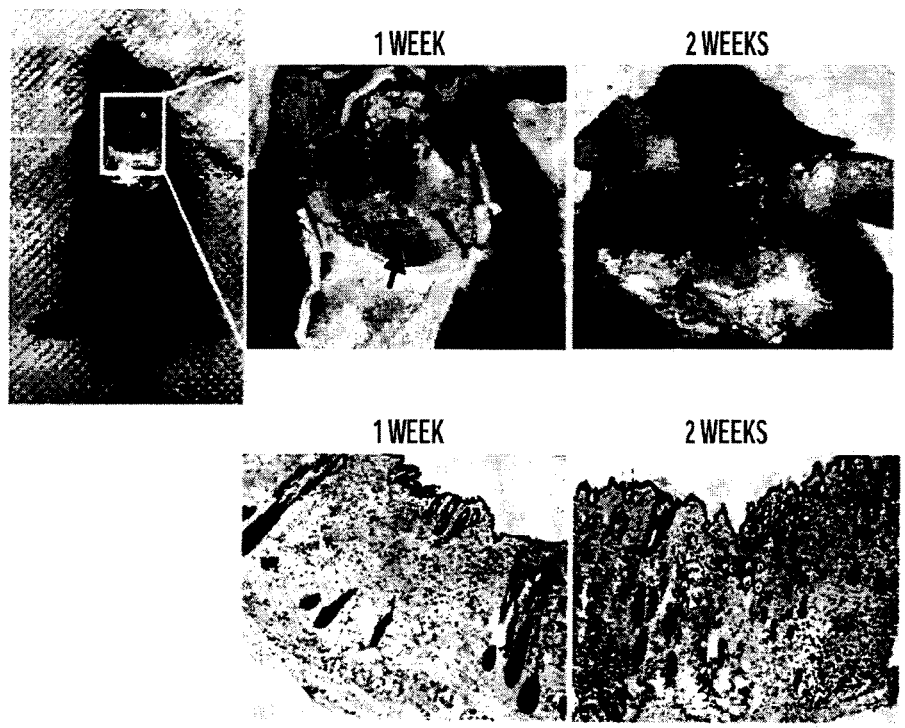
FIG. 7. Shows results for the injection of the semi-solid polymer (PCL-OE-1) subcutaneously in mice over 2 weeks. No visible tissue damage or inflammatory response was seen from the H&E stained tissue sections.
Figure 12:
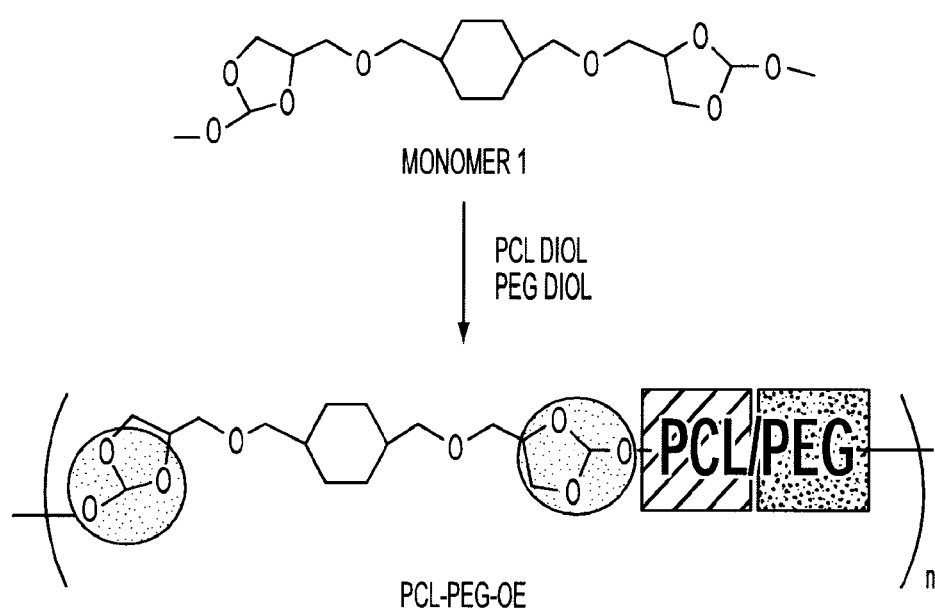
FIG. 12. Illustrates the synthesis of a representative polymer of the invention.
Figure 13:
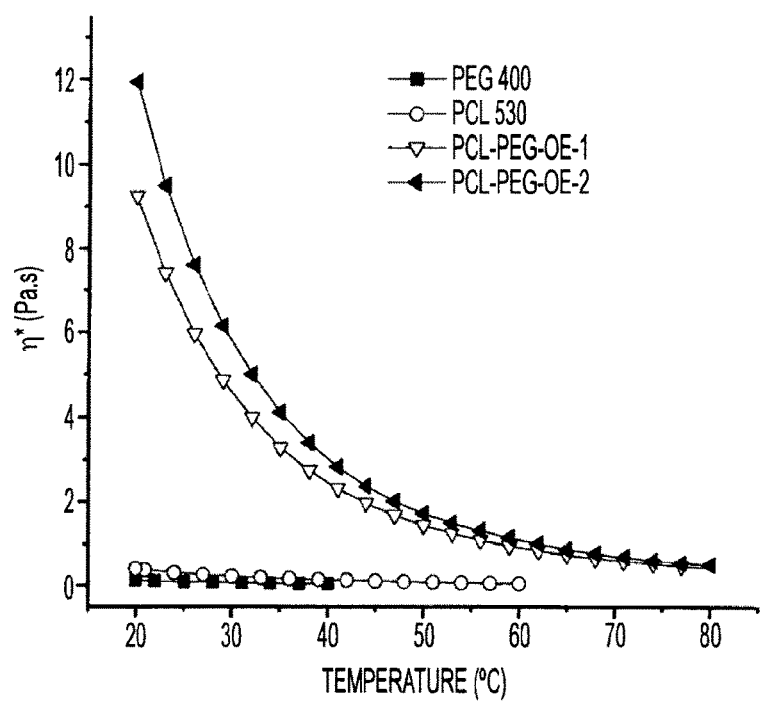
FIG. 13. Illustrates data from Example 3 that shows that the compound viscosity and temperature dependence of viscosity are dependent on polymer composition. Shear frequency was 1 Hz.
Figure 14:
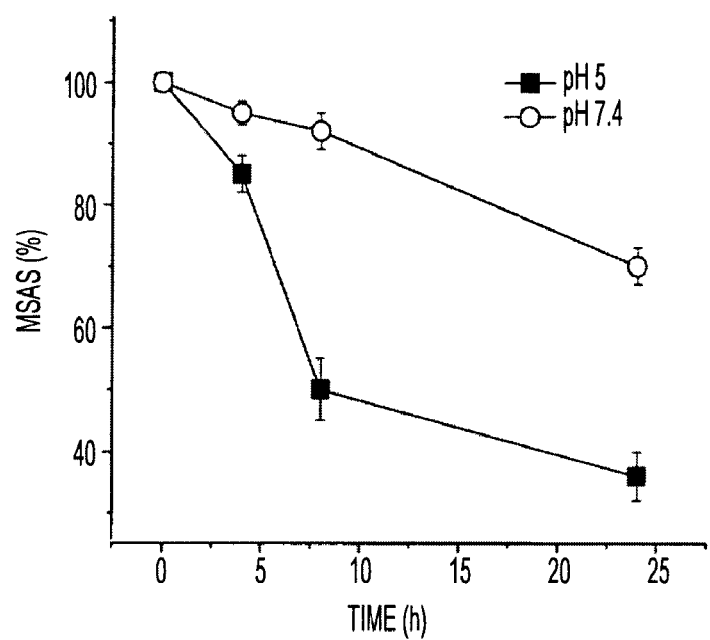
FIG. 14. Illustrates the mass loss of PCL-PEG-OE-1 in aqueous buffers of pH 7.4 and pH 5.0. Note that by the inclusion of PEG, the erosion rate of this polymer is much faster than PCL-OE-1. For PCL-PEG-OE-1, it only took one day to reach remaining mass of below 40%, whereas for PCL-OE-1, it took many days.
Figure 15:
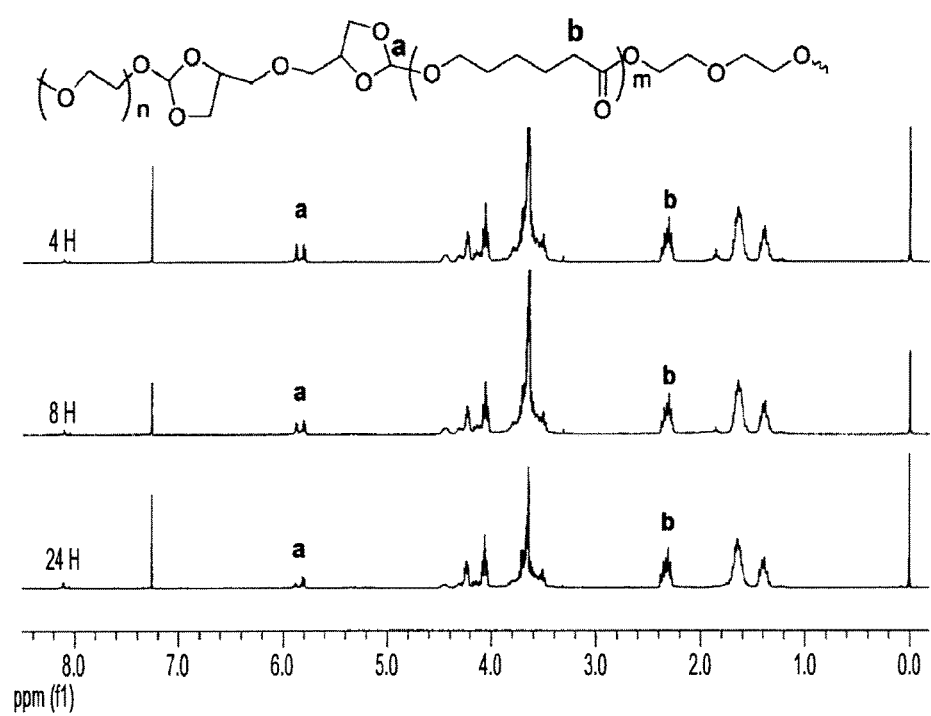
FIG. 15. Proton NMR analysis of PCL-PEG-OE-1 degradation in aqueous buffer of pH 5.0. As the ortho ester bond is cleaved, peak a diminishes substantially from 4 h to 24 h, whereas peak b of the PCL segment does not change significantly.
Figure 16:
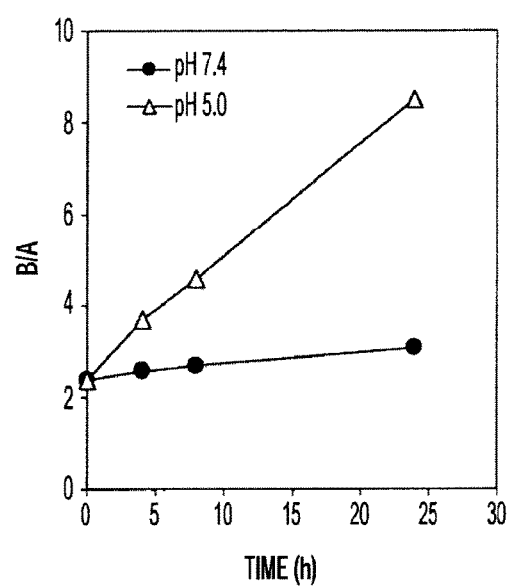
FIG. 16. Proton NMR analysis of PCL-PEG-OE-1 hydrolysis: the ratio of peak area b/a, representing the degree of ortho ester hydrolysis of the polymer, increased substantially with time at pH 5.0 but changed little over time at pH 7.4. This observation is consistent with the measurement of mass loss at different pHs (shown in FIG. 16).
Figure 17:
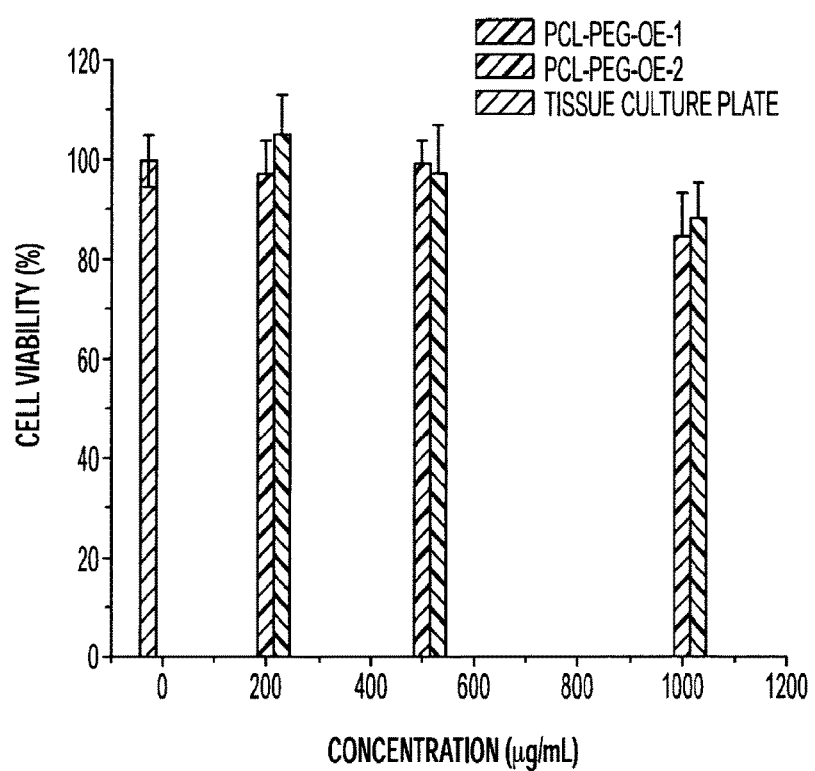
FIG. 17. Illustrates cytotoxicity data for the PCL-PEG-OE polymers. The polymers are essentially nontoxic even at concentrations as high as 1 mg/mL. The cytotoxicity test was conducted on NIH 3T3 mouse fibroblasts treated with polymers for 24 h FIG. 18. The PCL-PEG-OE polymers were dispersed in PBS buffer (pH 7.4) at 1 mg/mL and the average particle size of the suspensions was measured using dynamic light scattering. Because polymer 1 contained more PEG segment than polymer 2, it was able to form nanoparticles with diameter under 100 nm, which remained stable in pH 7.4 for at least 24 h. Therefore, the dispersion of the semi-solid polymer into large excess of aqueous buffer forming nanoparticles is a distinct feature of the PCL-PEG-OE polymers, which are amphiphilic in nature.
Figure 18:
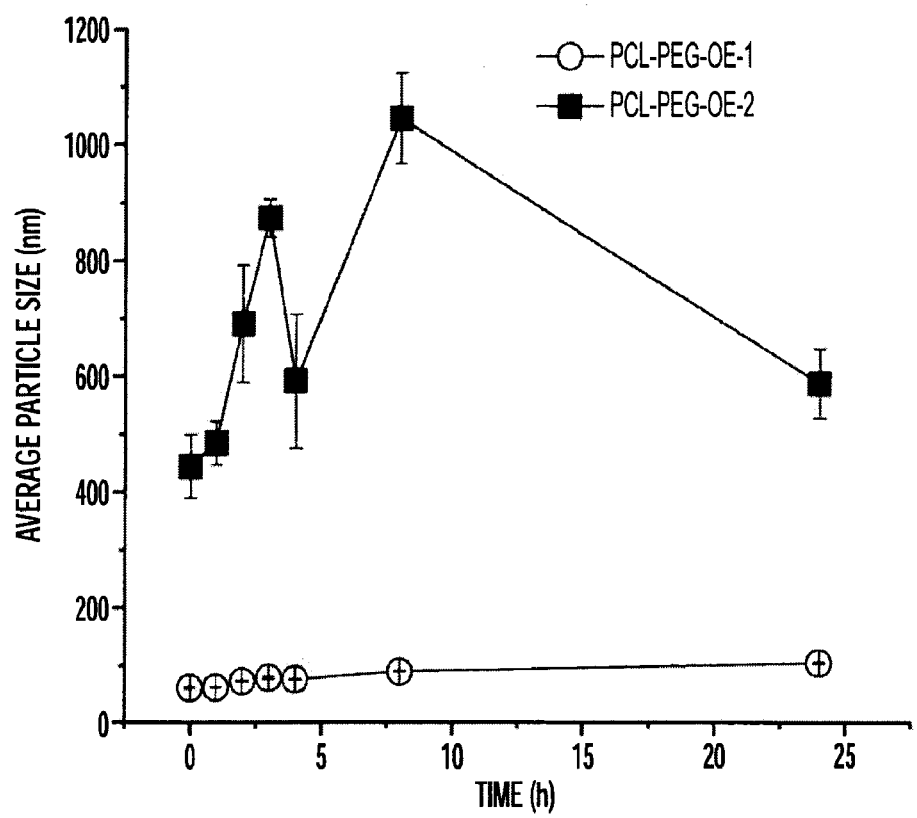
Figure 19:
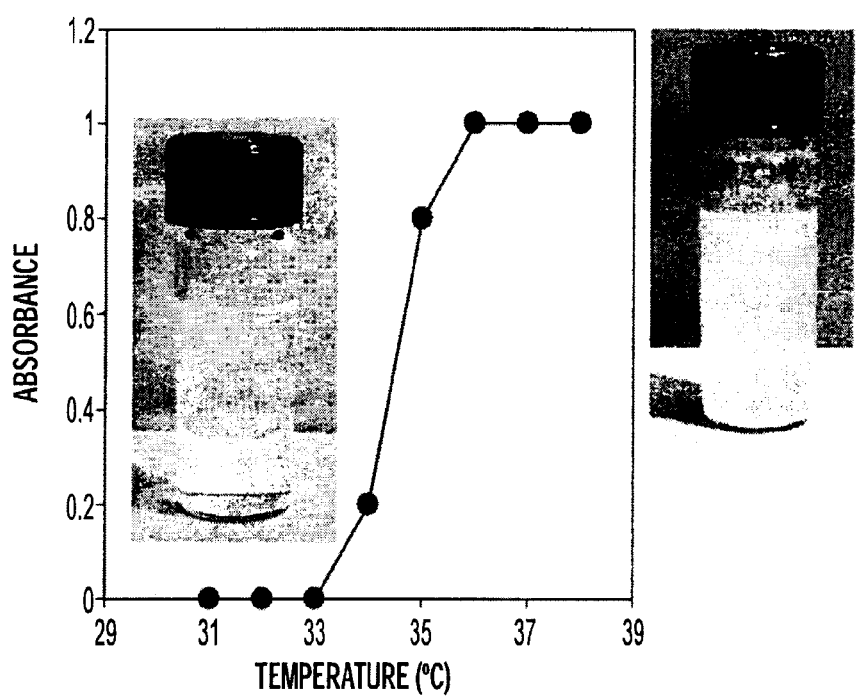
FIG. 19. PCL-PEG-OE-1 nanoparticles in water undergo temperature responsive phase transition. At temperature below ~35° C., the 1 mg/mL solution of the nanoparticles was optically clear, however, it turned cloudy as temperature raised up to 36° C. The temperature responsive phase transition behavior was also reversible. This temperature responsive behavior around the range of room temperature to physiological temperature is unique to the PCL-PEG-OE type of polymer; it was not observed with the PCL-OE polymers. This behavior suggests the possibility of using the nanoparticles as hyperthermia-controlled drug delivery vehicles.
Figure 20:
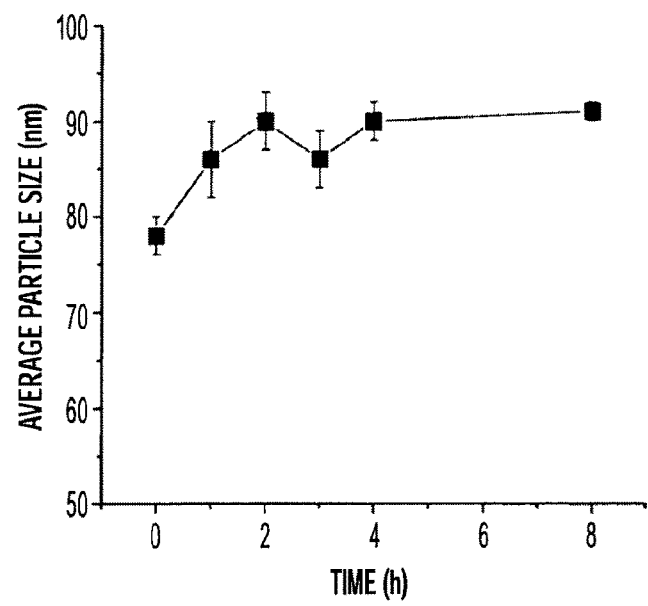
FIG. 20. Shows that Nile Red loaded PCL-PEG-OE-1 nanoparticles were smaller than 100 nm and remained stable in pH 7.4 aqueous buffer for at least 8 h, as observed by dynamic light scattering.

Processes and intermediates for preparing polymers of formula I are provided as further embodiments of the invention. Polymers of the invention can be prepared using techniques that are similar to those described herein or they can be prepared using techniques that are known. For example, polymers of the invention can be prepared using procedures similar to those that are described in Examples 1 and 3 and are illustrated in FIGS. 2, and 12. A compound with divicinyl diol such as 1,4-cyclohexanedimethanol bis (1,2-propane diol) ether (Compound 1, FIG. 1) was synthesized via hydrolysis of the corresponding 1,4-cyclohexanedimethanol diglycidyl ether with 100% conversion [Jiang, J.; Xiu, Z.; Hua, R. *Syn. Comm.* 2008, 38, 232-238.]. Compound 1 in THF with a trace amount of p-toluene sulfonic acid was reacted with an excess of trimethyl orthoformate at room temperature overnight to form 1,4-cyclohexanedimethanol bis(4-methanol-2-methyoxy-[1,3]-dioxolan) ether (Compound 2). Finally, the semi-solid polymer PCL-OE was synthesized by a transesterification reaction between Compound 2 and PCL diol (Mn 530) for 6 h at 135° C. in nitrogen. The product was collected and dialyzed against THF for 2 days to remove the unreacted monomers and catalyst, then dried under vacuum.

Representative polymers of the invention include polymers having the following structures:

-PCL-OE-PCL-OE-PCL-OE-PCL-

-PCL-OE-PEG-OE-PEG-OE-PCLwherein PCL is a unit comprising polycaprolactone; OE is a unit of formula Ia, IIa, or IIIa; and PEG is a unit comprising polyethylene oxide.

In one embodiment the invention provides polymers that comprise one or more units of formula Ib, IIb, or IIIb:

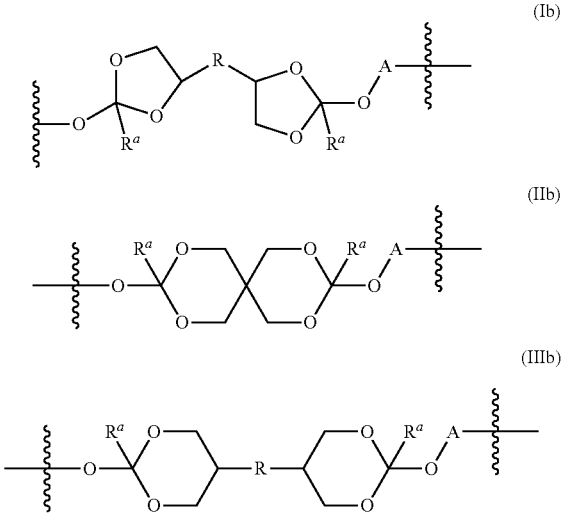

wherein each A is independently a unit comprising polycaprolactone. In one embodiment of the invention A is a homopolymer of caprolactone.

In one embodiment the invention provides polymers that comprise one or more units of formula Ic, IIc, or IIIc:

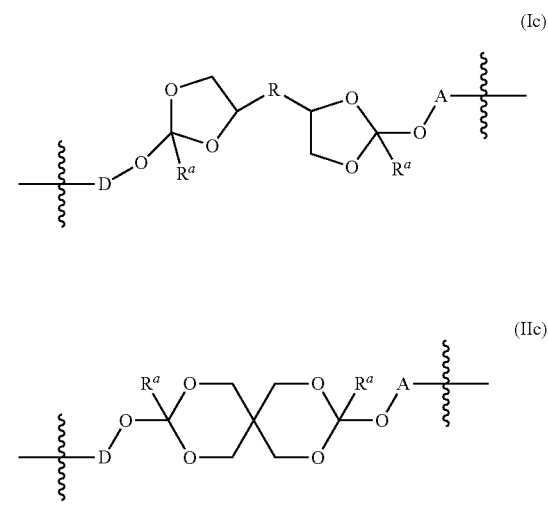

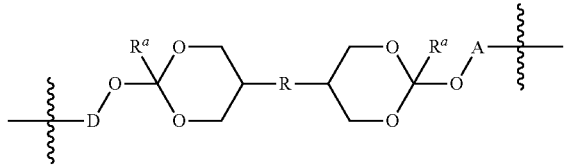

wherein each A is independently a polymer comprising polycaprolactone and each D is a unit comprising polyethylene oxide. In one embodiment of the invention A is a homopolymer of caprolactone. In one embodiment of the invention D is a homopolymer of ethylene oxide.

In one embodiment the polymers of the invention do not comprise one or more units of polyethyleneoxide.

In one embodiment the invention provides polymers that comprise one or more units of formula Ia.

In one embodiment the invention provides polymers that comprise one or more units of formula IIa.

In one embodiment the invention provides polymers that comprise one or more units of formula IIIa.

In one embodiment the invention provides polymers that comprise repeating units of formula Ib, IIb, or IIIb.

In one embodiment the invention provides polymers that comprise repeating units of formula Ic, IIc, or IIIc.

In one embodiment R is $(C_2-C_{10})$alkyl.

In one embodiment R is ethyl, propyl, butyl, pentyl, or hexyl.

In one embodiment R is ethyl, propyl, butyl, pentyl, or hexyl.

In one embodiment R is $(C_1-C_6)$alkyl$(C_3-C_8)$cycloalkyl $(C_1-C_6)$alkyl.

In one embodiment R is:

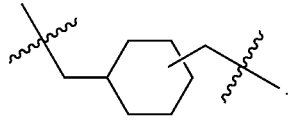

In one embodiment R is:

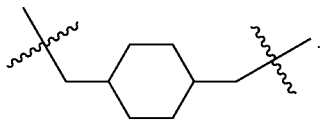 [SMILES: *CC1CCC(C*)CC1]

In one embodiment the invention provides polymers that comprise one or more units of formula:

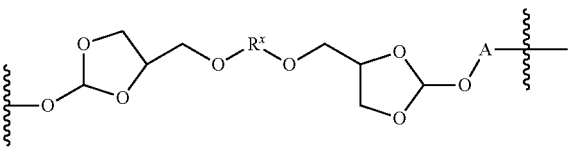

wherein $R^x$ is cyclohexyl or —$CH_2CH_2$—.

In one embodiment each R is independently $(C_1-C_{10})$ alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, or $(C_1-C_{10})$alkyl-O—$(C_1-C_{10})$alkyl.

In one embodiment each R is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, or $(C_1-C_{10})$alkyl-O—$(C_1-C_{10})$alkyl; and each A is independently a homopolymer or copolymer comprising polycaprolactone.

In one embodiment the polymer of the invention has a molecular weight of at least about 2000.

In one embodiment the polymer of the invention has a molecular weight of at least about 5000.

In one embodiment the polymer of the invention has a molecular weight of at least about 10,000.

In one embodiment the polymer of the invention has a molecular weight of less than about 50,000.

In one embodiment the polymer of the invention has a molecular weight of less than about 30,000.

In one embodiment the polymer of the invention has a molecular weight of less than about 20,000.

In one embodiment the polymer of the invention has a molecular weight of 15,000±10,000.

In one embodiment the polymer of the invention has a molecular weight of 15,000±5,000.

In one embodiment the polymer of the invention has a molecular weight of 20,000±5,000.

Polymers of the invention are useful as carriers for a variety of biologically active agents. The release of the biologically active agents from the polymers of the invention can be modified by blending the semi-solid polymer with buffer salts that control the pH environment. Another way is to control the molecular weight of the PCL segment. Yet another method is to change the structure of R. For example, in Example 1, the starting material 1,4-cyclohexanedimethanol diglycidyl ether can be replaced by 1,4-butanediol diglycidyl ether, and the resulting semi-solid polymer will have a faster degradation rate.

Units that Comprise Polycaprolactone

PCl can be synthesized via ring opening polymerization of caprolactone using well-known methods. See: Labet M, Thielemans W, Synthesis of polycaprolactone: a review. Chem Soc Rev. 2009, 38(12), 3484-3504. Many PCL diols are commercially available.

The invention provides polymers that have one or more ortho-ester containing units of formula Ia, IIa, or IIIa, and one or more units that comprise polycaprolactone.

In one embodiment of the invention the unit that comprises polycaprolactone is a homopolymer of caprolactone.

In one embodiment of the invention the unit that comprises polycaprolactone has the formula:

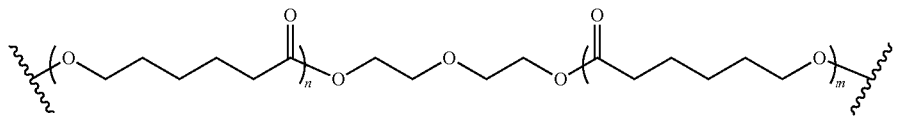

wherein n is an integer from 1-10 and m is an integer from 1-10.

In one embodiment of the invention the unit that comprises polycaprolactone is a copolymer of caprolactone and one or more other polymers that can be synthesized from ring opening polymerization.

In one embodiment of the invention the unit that comprises polycaprolactone can have the formula:

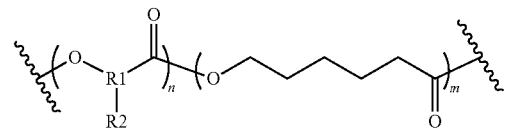

wherein: $R^1$ is $(C_1-C_{10})$alkyl, or $(C_1-C_{10})$alkenyl containing 1 to 3 double bonds; $R^2$ is hydrogen, $(C_1-C_{10})$alkyl, or $(C_1-C_{10})$alkenyl containing 1 to 3 double bonds, wherein the position at which $R^2$ is connected to $R^1$ can be at the α, β, γ, δ, ε, ζ carbon of $R^1$; m is an integer from 1-20; and n is an integer from 1-20.

In one embodiment of the invention at least 0.1 mol % of the unit that comprises polycaprolactone is polycaprolactone.

In one embodiment of the invention at least 1 mol % of the unit that comprises polycaprolactone is polycaprolactone.

In one embodiment of the invention at least 10 mol % of the unit that comprises polycaprolactone is polycaprolactone.

In one embodiment of the invention at least 25 mol % of the unit that comprises polycaprolactone is polycaprolactone.

In one embodiment of the invention at least 50 mol % of the unit that comprises polycaprolactone is polycaprolactone.

In one embodiment of the invention the molecular weight of the unit that comprises polycaprolactone is at least 50.

In one embodiment of the invention the molecular weight of the unit that comprises polycaprolactone is at least 100.

In one embodiment of the invention the molecular weight of the unit that comprises polycaprolactone is at least 150.

In one embodiment of the invention the molecular weight of the unit that comprises polycaprolactone is at least 500.

In one embodiment of the invention the molecular weight of the unit that comprises polycaprolactone is at least 1000.

In one embodiment of the invention the molecular weight of the unit that comprises polycaprolactone is 3000±2000.

In one embodiment of the invention the molecular weight of the unit that comprises polycaprolactone is less than 5000.

In one embodiment of the invention the molecular weight of the unit that comprises polycaprolactone is less than 3000.

In one embodiment of the invention the molecular weight of the unit that comprises polycaprolactone is less than 2000.

In one embodiment of the invention the molecular weight of the unit that comprises polycaprolactone is less than 1000.

In one embodiment of the invention "A" is a homopolymer of caprolactone.

In one embodiment of the invention "A" has the formula:

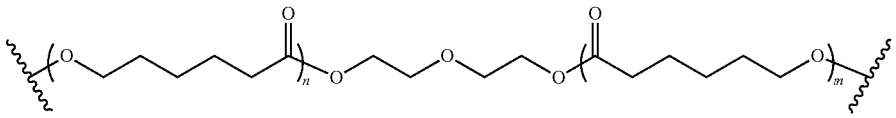

wherein n is an integer from 1-10 and m is an integer from 1-10.

In one embodiment of the invention "A" is a copolymer of caprolactone and one or more other polymers that can be synthesized from ring opening polymerization.

In one embodiment of the invention "A" can have the formula:

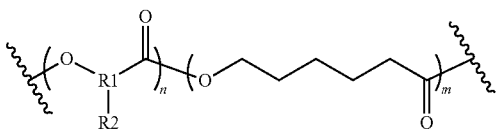

wherein: $R^1$ is $(C_1-C_{10})$alkyl, or $(C_1-C_{10})$alkenyl containing 1 to 3 double bonds; $R^2$ is hydrogen, $(C_1-C_{10})$alkyl, or $(C_1-C_{10})$alkenyl containing 1 to 3 double bonds, wherein the position at which $R^2$ is connected to $R^1$ can be at the α, β, γ, δ, ε, ζ carbon of R; m is an integer from 1-20; and n is an integer from 1-20.

In one embodiment of the invention at least 0.1 mol % of A is polycaprolactone.

In one embodiment of the invention at least 1 mol % of A is polycaprolactone.

In one embodiment of the invention at least 10 mol % of A is polycaprolactone.

In one embodiment of the invention at least 25 mol % of A is polycaprolactone.

In one embodiment of the invention at least 50 mol % of A is polycaprolactone.

In one embodiment of the invention at least 75 mol % of the unit that comprises polycaprolactone is polycaprolactone.

In one embodiment of the invention at least 90 mol % of the unit that comprises polycaprolactone is polycaprolactone.

In one embodiment of the invention at least 95 mol % of the unit that comprises polycaprolactone is polycaprolactone.

In one embodiment of the invention at least 99 mol % of the unit that comprises polycaprolactone is polycaprolactone.

In one embodiment of the invention the molecular weight of "A" is at least 50.

In one embodiment of the invention the molecular weight of "A" is at least 100.

In one embodiment of the invention the molecular weight of "A" is at least 150.

In one embodiment of the invention the molecular weight of "A" is at least 500.

In one embodiment of the invention the molecular weight of "A" is at least 1000.

In one embodiment of the invention the molecular weight of "A" is 3000±2000.

In one embodiment of the invention the molecular weight of "A" is less than 5000.

In one embodiment of the invention the molecular weight of "A" is less than 3000.

In one embodiment of the invention the molecular weight of "A" is less than 2000.

In one embodiment of the invention the molecular weight of "A" is less than 1000.

Units that Comprise Polvethyleneoxide (PEO or PEG)

The synthesis of PEG is well established in the literature, for example, see: J. Zhang, Y. Zhao, Z. Su, G. Ma, Synthesis of monomethoxy poly(ethylene glycol) without diol poly (ethylene glycol), J. Appl. Polym. Sci. 2007, 105(6), 3782-3786. Many PEG diols of various molecular weight are commercially available.

The invention provides polymers that have one or more ortho-ester containing units of formula Ia, IIa, or IIIa; one or more units that comprise polycaprolactone; and optionally one or more units that comprise polyethyleneoxide (PEO or PEG).

In one embodiment of the invention at least 0.1 mol % of the unit that comprises polyethyleneoxide is polyethyleneoxide.

In one embodiment of the invention at least 1 mol % of the unit that comprises polyethyleneoxide is polyethyleneoxide.

In one embodiment of the invention at least 10 mol % of the unit that comprises polyethyleneoxide is polyethyleneoxide.

In one embodiment of the invention at least 25 mol % of the unit that comprises polyethyleneoxide is polyethyleneoxide.

In one embodiment of the invention at least 50 mol % of the unit that comprises polyethyleneoxide is polyethyleneoxide.

In one embodiment of the invention at least 75 mol % of the unit that comprises polyethyleneoxide is polyethyleneoxide.

In one embodiment of the invention at least 90 mol % of the unit that comprises polyethyleneoxide is polyethyleneoxide.

In one embodiment of the invention at least 95 mol % of the unit that comprises polyethyleneoxide is polyethyleneoxide.

In one embodiment of the invention at least 99 mol % of the unit that comprises polyethyleneoxide is polyethyleneoxide.

In one embodiment of the invention the molecular weight of the unit that comprises polyethyleneoxide is at least 50.

In one embodiment of the invention the molecular weight of the unit that comprises polyethyleneoxide is at least 100.

In one embodiment of the invention the molecular weight of the unit that comprises polyethyleneoxide is at least 150.

In one embodiment of the invention the molecular weight of the unit that comprises polyethyleneoxide is at least 500.

In one embodiment of the invention the molecular weight of the unit that comprises polyethyleneoxide is at least 1000.

In one embodiment of the invention the molecular weight of the unit that comprises polyethyleneoxide is less than 2000.

In one embodiment of the invention the molecular weight of the unit that comprises polyethyleneoxide is less than 1000.

In one embodiment of the invention the molecular weight of the unit that comprises polyethyleneoxide is 500±250.

In one embodiment of the invention the molecular weight of the unit that comprises polyethyleneoxide is at least 50.

In one embodiment of the invention the molecular weight of the unit that comprises polyethyleneoxide is at least 100.

In one embodiment of the invention the molecular weight of the unit that comprises polyethyleneoxide is at least 150.

In one embodiment of the invention the molecular weight of D is at least 500.

In one embodiment of the invention the molecular weight of D is at least 1000.

In one embodiment of the invention the molecular weight of D is less than 2000.

In one embodiment of the invention the molecular weight of D is less than 1000.

In one embodiment of the invention the molecular weight of D is 500±250.

Biologically Active Agents

Polymers of the invention can be used to deliver a variety of biologically active agents. Examples of such agents include therapeutic agents (including small molecule drugs) and macromolecules (such as proteins, peptides, polysaccharides, and nucleic acids). For example, the polymers of the invention can be used to deliver agents that are useful for cancer therapy (anticancer drugs), anti-inflammatory therapy, anti-infectious therapy (such as antibiotics), neurological drug therapy including anesthetics for pain relief, antiangiogenic drugs, polysaccharides, vaccines, antigens, antibodies, cytokines, DNA and other polynucleotides, antisense oligonucleotides, RNA including small interfering RNA, and the like, and therapies to treat skin disorders and metabolic diseases such as diabetes. The polymers of the invention can also be used to deliver locally active agents such as astringents, antiperspirants, irritants, rubefacients, vesicants, sclerosing agents, caustics, escharotics, keratolytic agents, sunscreens and a variety of dermatologics including hypopigmenting and antipruritic agents. Other agents that can be delivered by this polymer includes biocides such as fungicides, pesticides, and herbicides, plant growth promoters or inhibitors, preservatives, disinfectants, air purifiers and nutrients. See for example U.S. Pat. No. 6,613,355.

Antigens that could be used at a dose of 1-1,000,000 μg or protein or cell number: antigens could include tumor cells (irradiated, frozen, lysed, dried), tumor-associated peptides, tumor neoantigens that result from genetic mutation in the somatic tumor cells, aberrantly glycolsylated tumor proteins, tumor cell membranes, or DNA encoding any of the above.

Adjuvants that could be used at a dose of 1-1,000,000 μg: toll-like receptor agonists such as but not limited to CpG, PolyIC, Imiquimod (or any imidazoquinoline-derivative of Imiquimod), Resiquimod, Flagellin.

The invention will now be illustrated by the following non-limiting Examples.

EXAMPLES

Example 1

Synthesis of 1,4-cyclohexanedimethanol bis(1,2-propane diol) ether

This is the precursor to monomer 1, which was used to synthesize PCL-OE-1. Ten grams of 1,4-cyclohexanedimethanol diglycidyl ether, 1.5 g of DI water and 1.5 g of DMF were sealed in a 20-mL ampoule. The ampoule was immersed into an oil bath of 140° C. for 24 hours. The product was dried at 40° C. under vacuum for 48 hours. (FIG. 1)

Synthesis of 1,4-cyclohexanedimethanol bis(4-methanol-2-methyoxy-[1,3]-dioxolan) ether This is monomer 1, which was used to synthesize PCL-OE-1. Five grams of 1,4-cyclohexanedimethanol bis(1,2-propane diol) ether, 50 mL of THF and trace amount of p-toluene sulfonic acid were added into a glass flask at room temperature. After all was completely dissolved, 25 g of trimethyl orthoformate was added dropwise to the flask. The reaction continued overnight. The THF was evaporated and the residual was dissolved in ethyl acetate, washed successively with saturated aqueous sodium bicarbonate and brine, dried over MgSO$_4$ and concentrated by evaporating the ethyl acetate. (FIG. 1)

Synthesis of 1,4-butanediol bis(1,2-propane diol) ether

This is the precursor to monomer 2, which was used to synthesize PCL-OE-2. Ten grams of 1,4-butanediol diglycidyl ether, 1.5 g of DI water and 1.5 g of DMF were sealed in a 20-mL ampoule. The ampoule was immersed into an oil bath of 140° C. for 24 hours. The product was dried at 40° C. under vacuum for 48 hours. (FIG. 1)

Synthesis of 1,4-butanediol bis(4-methanol-2-methyoxy-[1,3]-dioxolan) ether

This is monomer 2, which was used to synthesize PCL-OE-2. Five grams of 1,4-butanediol bis(1,2-propane diol) ether, 50 mL of THF and trace amount of p-toluene sulfonic acid were added into a glass flask at room temperature. After all was completely dissolved, 25 g of trimethyl orthoformate was added dropwise to the flask. The reaction continued overnight. The THF was evaporated and the residual was dissolved in ethyl acetate, washed successively with saturated aqueous sodium bicarbonate and brine, dried over MgSO$_4$ and concentrated by evaporating the ethyl acetate. (FIG. 1)

Synthesis of semi-solid poly(ortho ester caprolactone): PCL-OE-1

Three grams of monomer 1 and 4.2 g of PCL diol (Mw 530, Sigma) were added into a flask and 1 weight % of pyridinium p-toluene sulfonic acid were added to the reaction system as catalyst. The reaction continued for 6 h at 135° C. in nitrogen atmosphere. The product was collected and dialyzed against THF for 2 days to remove unreacted monomers and catalyst. The final product was obtained after vacuum drying. (FIG. 1)

Synthesis of semi-solid poly(ortho ester caprolactone): PCL-OE-2

2.6 grams of monomer 2 and 4.2 g of PCL diol (Mw 530, Sigma) were added into a flask and 1 weight % of pyridinium p-toluene sulfonic acid were added to the reaction system as catalyst. The reaction continued for 6 h at 135° C. in nitrogen atmosphere. The product was collected and dialyzed against THF for 2 days to remove unreacted monomers and catalyst. The final product was obtained after vacuum drying. (FIG. 1)

Characterizations

¹H NMR spectra were recorded on a Varian Unity spectrometer (300 MHz) with CDCl₃ as solvent. Molecular weight of the polymer was measured on a GPC equipment with THF as solvent. Differential Scanning Calorimetry (DSC) was carried out over a temperature range of 100° C. to 150° C. using a TA Q100 calorimeter purged with nitrogen. The heating or cooling rate was 10° C./min. The midpoint of the transition zone was taken as the glass transition temperature ($T_g$). Hydrolytic degradation behavior of synthesized injectable polymers was conducted in buffer solutions of both pH 7.4 and pH 5 at 37° C. The original weight of the sample was recorded as $W_0$. At certain time point, sample was taken out and its dry weight was recorded as $W_1$. And the weight loss ($W_{loss}$) was calculated from $100(W_0-W_1)/W_0$. Triplicates were conducted for each time point and the average values were reported.

Rheology

The rheological behavior of the polymers was measured with an AR-G2 rheometer (TA Instrument, Ltd) equipped with parallel plate geometry (25 mm diameter). The gap between parallel plates was adjusted to around 1 mm. The dynamic strain sweep measurement was first performed to ensure that the materials were in their linear viscoelastic range and then the small amplitude oscillatory shear was conducted over a temperature range of 20° C. to 80° C.

Cytocompatibility Evaluation

The cytocompatibility of the semi-solid polymers was evaluated by an MTT (3-(4,5-dimethyl-thiazol-2-yl)-2,5-diphenyl tetrazolium bromide) assay. Fibroblast cells (NIH3T3) were seeded into 96-well plates at 10000 cells/well and cultured with polymers of various concentration for 24 hours in Dulbecco's Modified Eagle Medium supplemented with 10% FBS, 10 mM HEPES, 100 U/mL penicillin/streptomycin at 5% $CO_2$ and 37° C. MTT in PBS (5 mg/mL, 20 mL) was added to each well reaching a final concentration of 0.5 mg/mL. After 4 hours, unreacted MTT was removed by aspiration. The formazan crystals were dissolved in 100 L of DMSO and the absorbance was measured at 570 nm using a Bio-Tek Synergy HT plate reader. Cell viability was calculated by [Absorbance of cells exposed to polymer]/[Absorbance of cells cultured without polymer] in percentage.

Drugs Loading and Release

A certain amount of drugs (Ibuprofen or BSA) were grinded into fine particles and then mixed with certain amount of polymer in a glass vial. The mixtures were manually stirred for about 20 minutes and then place on the bench overnight before use. The drug release behavior of polymers was measured as the following: around 50 mg of drug loaded polymer (5 wt %) was placed in small nylon bags (200 mesh) and immersed in 6 mL of buffered saline (pH 7.4 or 5.0). At certain time points, the buffer was removed for analysis and replaced with fresh buffer. The amount of Ibu released in the medium was measured by UV spectroscopy (Beckman Coulter, DU 640B spectrophotometer) for absorbance at 263 nm. The BSA concentration was measured by the absorbance at 595 nm with a Quick Start™ Bradford Protein Assay kit.

In Vivo Biocompatibility Evaluation

In vivo biocompatibility of the polymer was evaluated by subcutaneous injection into mice through 18-gauge needles; 50 mg of polymer was injected for each mouse. At certain time point, mouse was sacrificed and the tissue of the injection site harvested, sectioned, and stained with H&E.

Results

The Feed composition, average molecular weight, and glass transition temperature of the semi-solid polymers prepared in Example 1 are provided in Table 1.

TABLE 1

Feed composition, average molecular weight, and glass transition temperature of the semi-solid polymers.

| Polymer samples | PCL diol (g) | Monomer 1 (g) | Monomer 2 (g) | $M_w$ | $M_n$ | $T_g$ (° C.) |
|---|---|---|---|---|---|---|
| POE-CL-1 | 4.2 | — | 3.0 | 13650 | 6500 | −51 |
| POE-CL-2 | 4.2 | 2.6 | — | 19090 | 8300 | −58 |

Molecular weight determined by GPC.
$T_g$ determined by DSC.

Analytical data and assay results for the compounds prepared in Example 1 are shown in FIGS. 1-7.

An anti-inflammatory drug, Ibu, was loaded into the semi-solid polymer (PCL-OE-1) by simple dissolution. Ibu is a small molecular drug with poor solubility in water. The semi-solid polymer, on the other hand, provides excellent solubility for Ibu, resulting in a clear solution. A model protein drug, BSA, is highly water soluble, and was also incorporated with the semi-solid polymer by mixing fine particles of the protein. The opaque suspension of BSA particles in the semi-solid polymer maintained excellent injectability.

Example 2

Sustaining Tumoricidal T Cell Responses with Polymer Vaccine Delivery Platform Vaccines have recently been approved by the FDA for the prevention of cervical cancer and treatment of castration-resistant prostate cancer. Despite these early success stories, the majority of cancer vaccines tested in clinical trials have generated modest clinical responses and suboptimal immune responses. The vast majority of these vaccines involve acute injection of tumor antigen and immune adjuvant that is rapidly degraded. This acute delivery approach has yielded low-level and transient tumor-reactive T cells frequencies and weak antibody titers, relative to real viral infections that prime massive immune responses and take days-to-weeks to clear. The biodegradable polymers of the invention can be used to provide a sustained delivery vaccine similar to a real viral infection, resulting in more robust and long-lasting T and B cell responses.

Methods

Animal Models

Female C57BL/6 (BL6) mice (6-8 weeks old) were purchased from Jackson Laboratory and maintained in a specific pathogen-free facility according to the guidelines of the University of Minnesota Animal Care and Use Committee.

Vaccine Preparation

As standard delivery methods for comparison, soluble ovalbumin (OVA) protein, a model antigen, and Resiquimod (RES) were delivered in 1% DMSO in phosphate buffered saline (PBS). Semi-solid polymer (PCL-OE-1) formulations were prepared by mixing lyophilized OVA powder with the polymer to generate a dispersion. RES was directed dissolved into the semi-solid polymer. The antigen/adjuvant formulation was mixed by stirring for 10 min and allowed to settle overnight at 4° C. before use.

Immunization Protocol

Mice were vaccinated subcutaneously in the right inguinal region with either 50 µL of either 0.9% saline once daily for four consecutive days, OVA protein (200 µg) plus RES (50 µg) in 1% DMSO once daily for four consecutive days, or a single injection with semi-solid polymer plus OVA (800 µg) and RES (200 µg). All formulations were freshly prepared at the time of vaccination.

Flow Cytometry

A total of 50 µL of whole blood was stained with MHC class I-OVA dextramer (Immundex) at 4° C. for 30 minutes followed by staining with PerCp-Cy5.5-conjugated anti-CD8 (eBioscience) at 4° C. for 1 hour. Red blood cells were lysed and cells were washed twice with PBS and re-suspended in FACS buffer followed by analysis using a FACSCanto II. Data were further analyzed with FlowJo software (Tree Star). Plots were generated from Prism (GraphPad Software, Inc). Analysis gates were set based on the PerCp-Cy5.5 positive population. The percentage of OVA-specific CD8 T-cells was calculated based on the percentage of cells stained with MHC-I/OVA dextramer within the CD8+ population.

4ELISA to Quantify OVA Antibody Response

OVA protein was plated at 0.5 µg/ml in PBS (100 µL/well) in 96-well flat bottom plates and incubated overnight at 4° C. Each well was washed with 2% fraction V BSA/PBS (100 µL/well) for 60 min at room temperature. Wells were then washed once with 0.5% fraction V BSA/PBS (200 µL/well). Plasma samples were then added to the wells at a 1:300 dilution in PBS (100 µL/well) and incubated for 2 h at room temperature. Wells were then washed three times with 0.5% fraction V BSA/PBS (200 µL/well) and once with PBS (200 µL/well). 100 µL of a 1:2500 mouse polyclonal alkaline phosphatase-conjugated secondary antibody in PBS was added to each well and incubated for 1 hour at room temperature. Wells were then washed three times with 0.5% fraction V BSA/PBS (200 µL/well) and once with PBS (200 µL/well). 100 µL of a 1 mg/mL p-nitrophenyl phosphate/diethanolamine buffer solution (Thermo Scientific) was added to each well. The reaction was allowed to proceed at room temperature in the dark for 15 min and then absorbance was read at 405 nm.

Blood/Plasma Collection

Blood was collected from the periorbital vein on days 5, 7, 9, 13, 20, 27, 34, 48, 62, 77 and 100. Mice were anesthetized with 75 mg/kg i.p. for the procedure and monitored closely throughout. After collection, proparacaine 1% eye drops and triple antibiotic ointment were applied to the collection site. At each time point, 100 µL of whole blood was diluted in 50 µL of heparin (1000 units/mL). Plasma samples were prepared from 50 µL of whole blood as described. The remaining 50 µL was used the same day for flow cytometry experiments.

Plasma was collected from whole blood by dilution in 50 µL (1000 unit/mL) heparin. Samples were allowed to sit at room temperature for 30 min after addition of heparin, followed by centrifugation for 15 min at room temperature at 2000 g. Samples were stored at −80° C. until use.

Results

Figure 8:
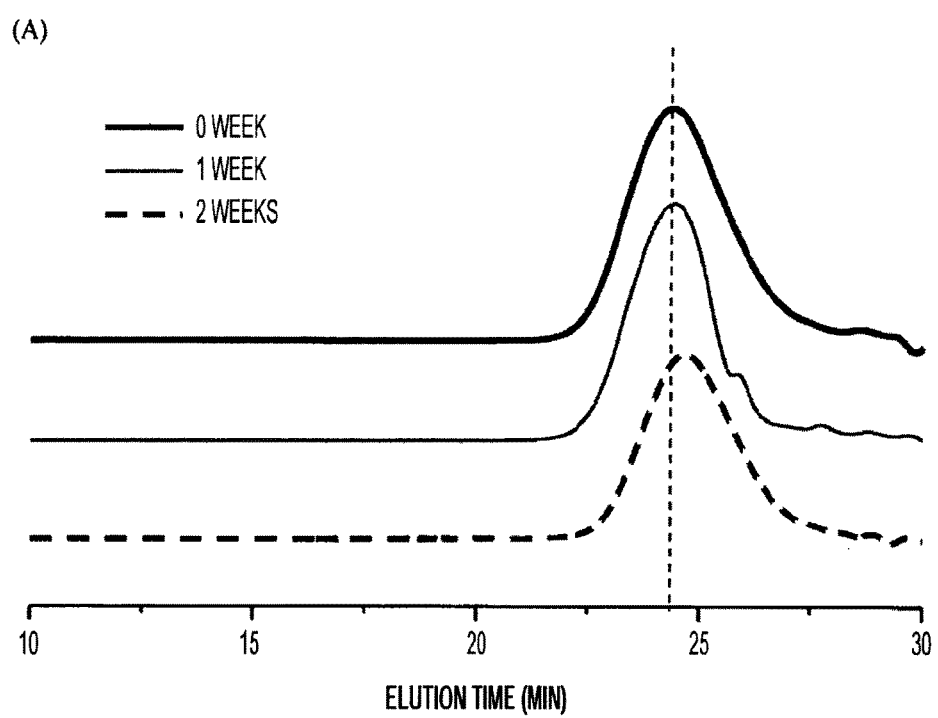
FIG. 8. (A) GPC traces of semi-solid samples after 1 and 2 weeks of implantation in mice. After 1 week some of the short chain polymers were lost but the majority of the polymer was yet to degrade. After 2 weeks there was marked degradation of the polymer, resulting in a shift in the peak position and the appearance of short polymer chains; (B) Proton NMR analysis of the semi-solid polymer after 1 and 2 weeks of implantation in mice. Shown are characteristic peaks of ortho ester protons (h) and PCL protons (e). The ortho ester bond and the PCL structure in the remaining polymer are largely intact. The ability of maintaining structural stability in vivo for considerable amount of time supports the utility of the polymer for sustained drug delivery.
Figure 8:
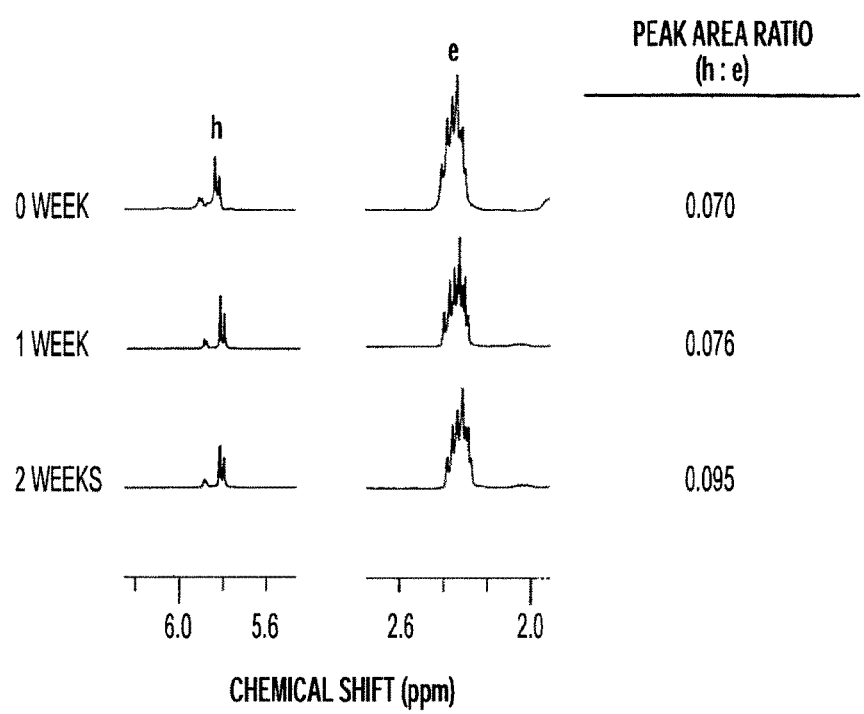
Figure 9:
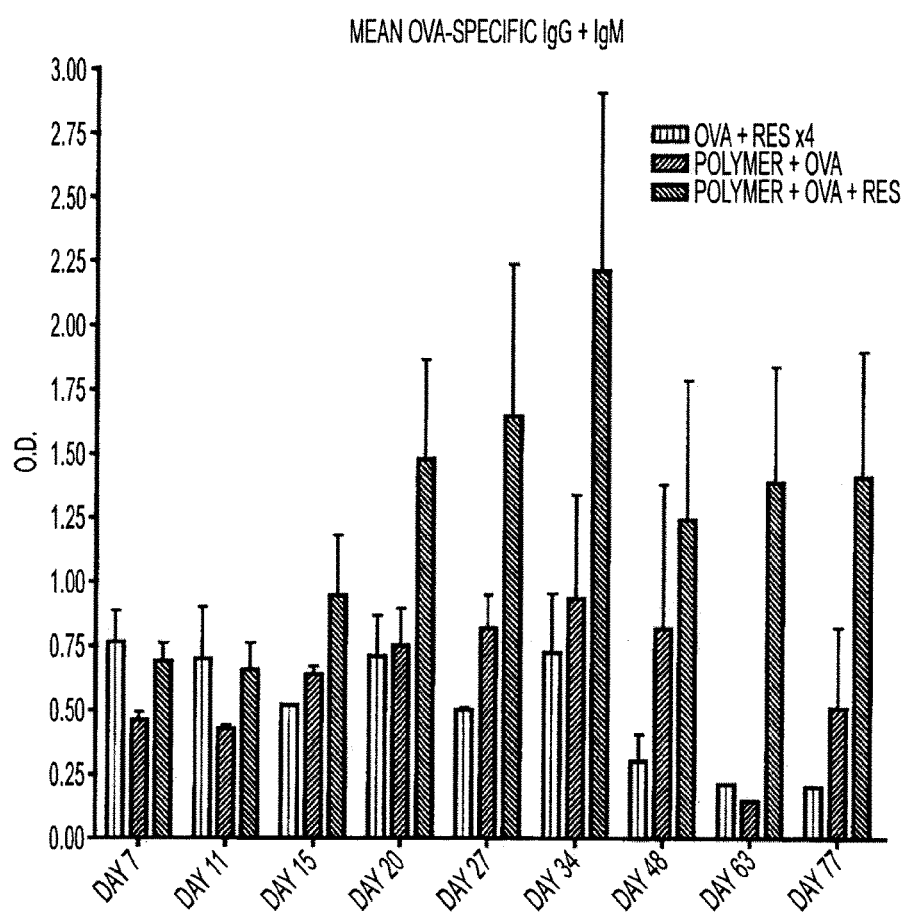
FIG. 9. Illustrates antigen-specific antibody response following administration of a composition comprising a polymer of the invention and a combination of OVA and RES. Mice treated with the combination of OVA and RES delivered via the semi-solid polymer had high intensity and sustained antibody responses through at least day 77. Antibodies are key factors in the generation and maintenance of helper T-cell responses. CD4+ helper T-cells have been shown to play a critical role in the therapeutic immune response, having demonstrated cytolytic activity. CD4 cells can be more efficient at tumor rejection than CD8 cells.
Figure 10:
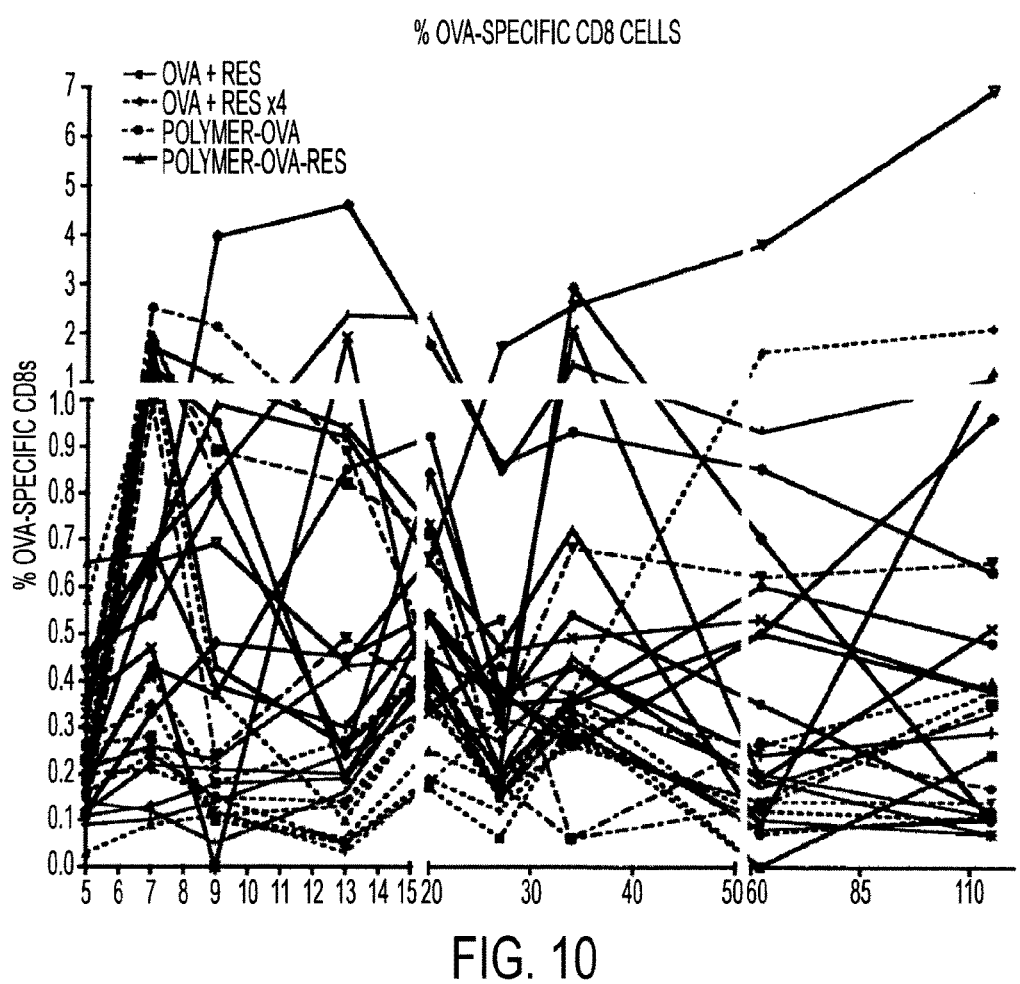
FIG. 10. Illustrates antigen-specific CD8 T cell response following administration of a composition comprising a polymer of the invention and a combination of OVA and RES. Mouse to mouse variability in the intensity and duration of immune response is found within all the treatment groups. However, a number of mice (5/12) in the polymer group showed maintenance of OVA-specific CD8 T-cells above standard treatment levels at 4 months post-vaccination. Even more encouraging is the upward trend in % OVA-specific CD8 cells in 4/5 of those mice on day 115. Sustainment of recall response and cytolytic ability are currently being tested.
Figure 11:
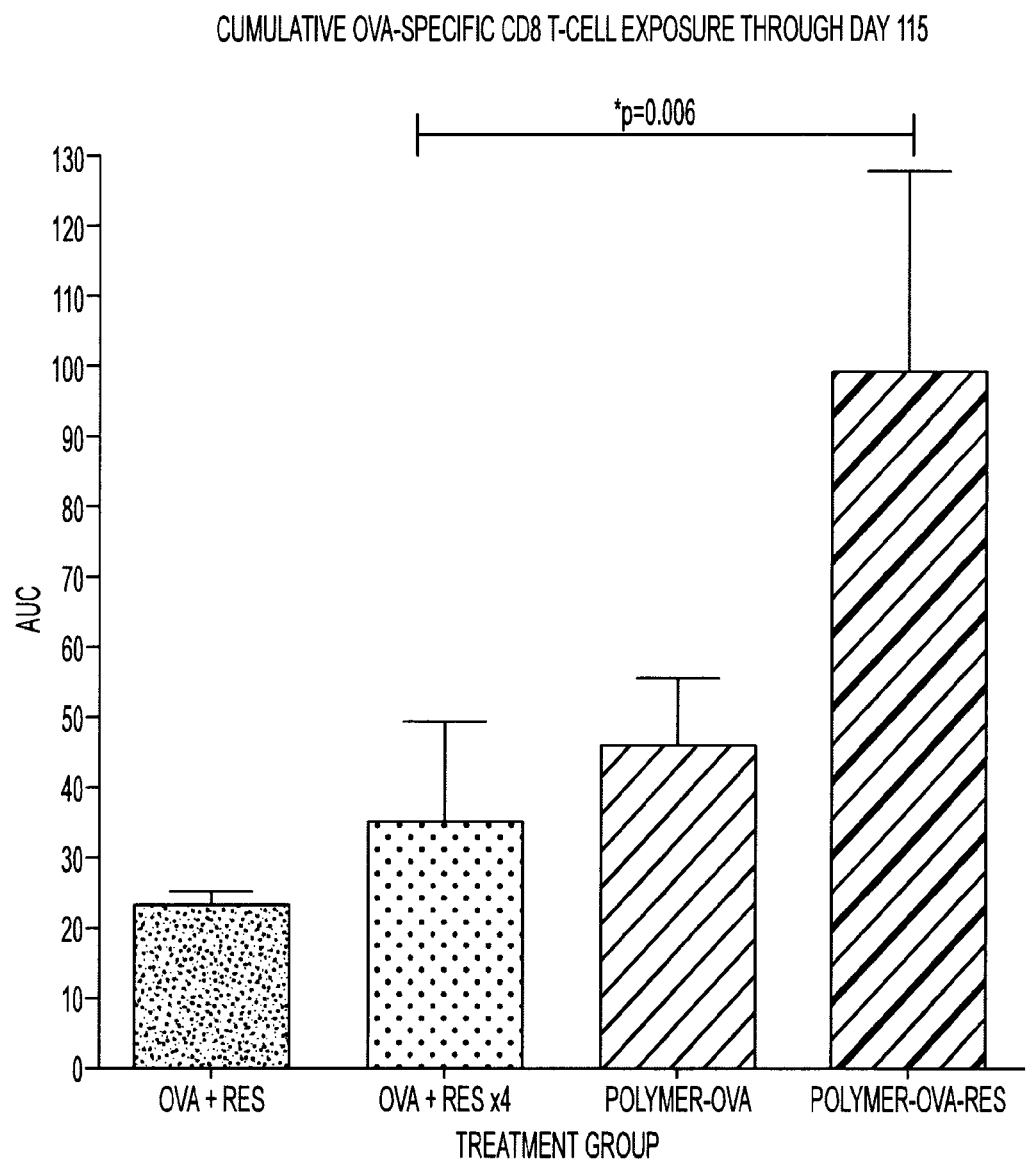
FIG. 11. Illustrates antigen-specific CD8 T cell response following administration of a composition comprising a polymer of the invention and a combination of OVA and RES. The data in FIG. 11 was analyzed by calculating area under the curve (AUC) from day 0 through day 115 for each mouse. The results represent the average cumulative exposure to OVA-specific CD8+ T-cells in each group. In a therapeutic setting, total exposure to cytotoxic T-cells may prove to be an important predictor of treatment outcome, which makes the analysis of AUC here more meaningful and informative. It is clearly seen here that the single injection of semi-solid formulation of the antigen and adjuvant achieved significantly higher T cell response than all other treatment groups.

Results from Example 2 for the compounds prepared in Example 1 are shown in FIGS. 8-10.

Example 3

Methods

Synthesis of Semi-Solid Polymers: PCL-PEG-OE-1 and PCL-PEG-OE-2

3.5 grams of monomer 1, 2.65 g of PCL diol (Mw 530, Sigma), 2 g of PEG diol (Mw 400, Sigma, at PCL/PEG molar ratio of 1,) were added into a three-neck flask with a condensing column, and 1 weight % of pyridinium p-toluene sulfonic acid were added to the reaction system as catalyst. The reaction continued for 4 hours at 135° C. under stirring in nitrogen atmosphere and then continued for another 2 hours at 135° C. under reduced pressure. The product was cooled down and dissolved into 400 mL THF. A few drops of TEA was added to THF to keep the environment a little bit of alkaline. The product was dialyzed against THF with cut off molecular weight 1000 Da for 2 days to remove unreacted monomers and catalyst. The final product was obtained after vacuum drying. The final product was synthesized with a feed molar ratio of PCL/PEG of 1, hence named "PCL-PEG-OE-1". Using the same procedure another polymer was also synthesized with a feed molar ratio of PCL/PEG of 2, hence named "PCL-PEG-OE-2". In both cases, the molar ratio of monomer 1 and the sum of PCL and PEG was kept constant as 1. The synthesis is illustrated in Figure The resulting polymers were characterized by GPC, proton NMR, rheology, erosion (by mass loss), and cytotoxicity (MTT assay), using procedures similar to those described in Example 1.

Polymer Nanoparticle Formation and Characterization of Size and Temperature Sensitivity 3 mg of the PCL-PEG-OE polymers were mixed with 3 mL of PBS (pH 7.4) at room temperature and the average hydrodynamic diameter of the nanoparticles was determined using a ZetaPlus Particle Analyzer (Brookhaven Instruments Corporation, Holtsville, N.Y.; 27 mW laser; 658 nm incident beam, 90° scattering angle). The optical transparency of the nanoparticle solution was measured by UV-Vis light spectroscopy at 500 nm with a heating rate of ~1° C. per minute.

Solubilization of Poorly Water Soluble Molecules

Nile Red (NR, 3 mg) was dissolved in 100 mg of PCL-PEG-OE-1 polymer and mixed well. After incubating at room temperature overnight, the 3% NR loaded polymer was mixed with 3 mL of PBS (pH 7.4). The nanoparticle solution was photographed and the average particle size of the NR loaded nanoparticles was measured by dynamic light scattering as described above.

Results

The Feed composition, average molecular weight, and glass transition temperature of the semi-solid polymers prepared in Example 3 are provided in Table 2.

TABLE 2

Feed composition, average molecular weight, and glass transition temperature of the semi-solid polymers.

| Polymer samples | PCL diol (mol) | PEG diol (mol) | Monomer 1 (mol) | $M_n$ | $M_w$ |
|---|---|---|---|---|---|
| PCL-PEG-OE-1 | 1 | 1 | 2 | 2752 | 4943 |
| PCL-PEG-OE-2 | 2 | 1 | 3 | 2286 | 4607 |

Molecular weight determined by GPC.

Analytical data and assay results for the compounds prepared in Example 3 are shown in FIGS. 11-20.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polymer comprising 1) one or more units of formula Ia:

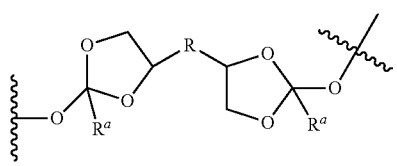
(Ia)

and 2) one or more units of formula:

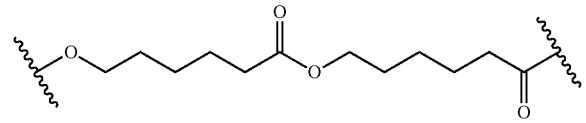

or formula:

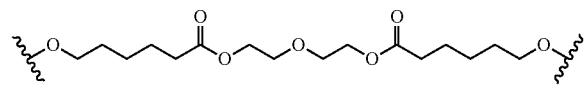

wherein:

each R is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl $(C_1-C_6)$alkyl, aryl$(C_1-C_{10})$alkyl, $(C_1-C_6)$alkyl-O—$(C_1$-$C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1$-$C_6)$alkyl-$(C_3-C_8)$cycloalkyl-$(C_1-C_6)$alkyl-O—$(C_1-C_6)$alkyl, or $(C_1-C_{10})$alkyl-O—$(C_1-C_{10})$alkyl; and each $R_a$ is independently hydrogen, $(C_1-C_{10})$alkyl, $(C_3$-$C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, or $(C_1-C_{10})$alkyl-O—$(C_1-C_{10})$alkyl.

2. The polymer of claim 1 which comprises one or more units of formula Ib:

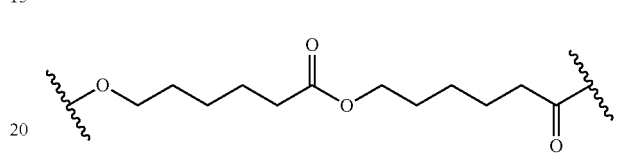
(Ib)

wherein each A independently comprises one or more units of formula:

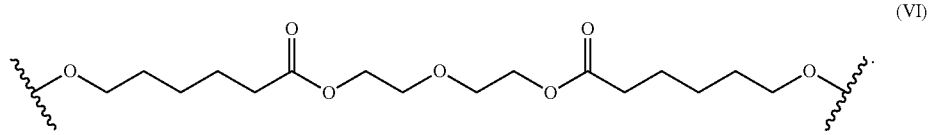

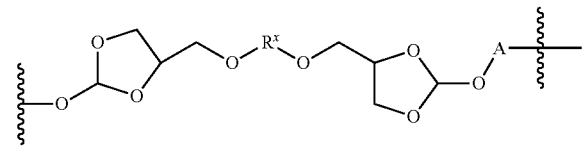
(VI)

3. The polymer of claim 2 which consists of repeating units of formula Ib.

4. The polymer of claim 2 which comprises one or more units of formula:

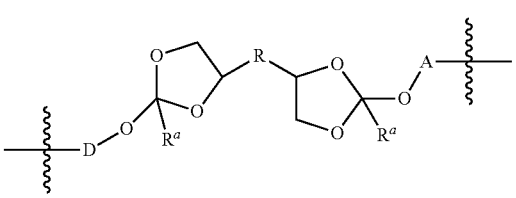

wherein $R^x$ is cyclohexyl or —$CH_2CH_2$—.

5. The polymer of claim 2 wherein each R is independently $(C_1-C_{10})$alkyl, $(C_3-C_8)$cycloalkyl, $(C_1-C_6)$alkyl$(C_3$-$C_8)$cycloalkyl, $(C_3-C_8)$cycloalkyl$(C_1-C_6)$alkyl, $(C_1-C_6)$alkyl $(C_3-C_8)$cycloalkyl$(C_1-C_6)$alkyl, aryl$(C_1-C_{10})$alkyl, or $(C_1$-$C_{10})$alkyl-O—$(C_1-C_{10})$alkyl; and each A is independently a homopolymer or copolymer comprising one or more units of formula V or formula IV.

6. The polymer of claim 1 which comprises one or more units of formula Ic:

(Ic)

wherein each A independently comprises one or more units of formula:

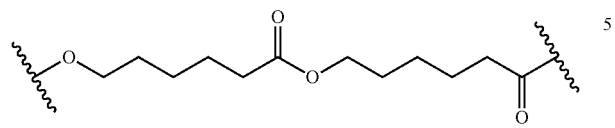

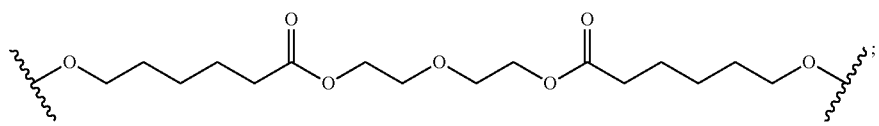

and each D is a unit comprising polyethylene oxide.

7. The polymer of claim 6 which consists of repeating units of formula Ic.

8. The polymer of claim 1 wherein R is $(C_2-C_{10})$alkyl.

9. The polymer of claim 1 wherein R is ethyl, propyl, butyl, pentyl, or hexyl.

10. The polymer of claim 1 wherein R is $(C_1-C_6)$alkyl $(C_3-C_8)$cycloalkyl$(C_1-C_6)$alkyl.

11. The polymer of claim 1 wherein R is:

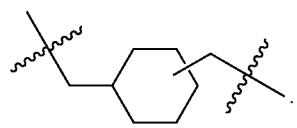

12. The polymer of claim 1 wherein R is:

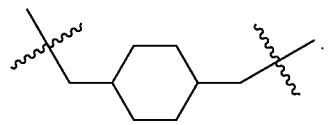 [SMILES: *CC1CCC(C*)CC1]

13. The polymer of claim 1 that comprises one or more units that comprise polyethylene oxide.

14. A polymer comprising 1) one or more units of formula Ia:

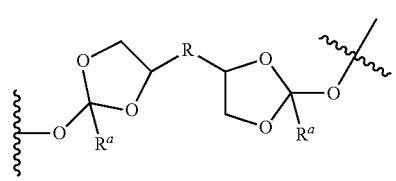

(Ia)

and 2) one or more units of the following formula:

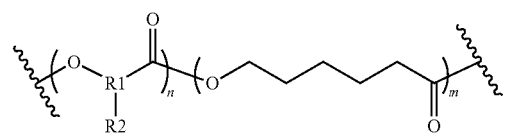

wherein:

each $R_a$ is independently hydrogen, $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, or $(C_1-C_{10})$alkyl-O—$(C_1-C_{10})$alkyl;

$R^1$ is $(C_1-C_{10})$alkyl, or $(C_1-C_{10})$alkenyl containing 1 to 3 double bonds;

$R^2$ is hydrogen, $(C_1-C_{10})$alkyl, or $(C_1-C_{10})$alkenyl containing 1 to 3 double bonds, wherein the position at which $R^2$ is connected to $R^1$ can be at the $\alpha,\beta,\gamma,\delta,\varepsilon,\zeta$ carbon of $R^1$;

m is an integer from 1-20; and n is an integer from 1-20.

15. A pharmaceutical composition comprising a polymer of claim 1 and a biologically active agent.

16. The composition of claim 15 wherein the biologically active agent is a small molecular drug, large molecular drug, protein, antibody, peptide, polysaccharide, or nucleic acid.

17. A polymer comprising 1) one or more units of formula Ia:

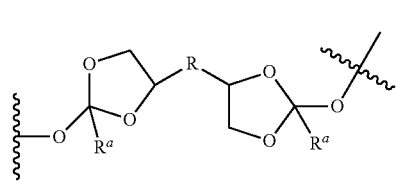

(Ia)

and 2) one or more units of the following formula:

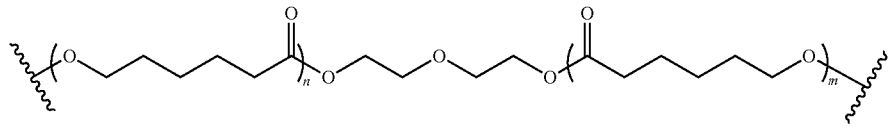

10 wherein:
each R is independently $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, $(C_1-C_6)$alkyl-O—$(C_1-C_6)$alkyl-O—$(C_1-C_6)$alkyl, $(C_1-C_6)$alkyl-O—$(C_3-C_8)$cycloalkyl-O—$(C_1-C_6)$alkyl, $(C_1-C_6)$alkyl-O—$(C_1-C_6)$alkyl—$(C_3-C_8)$cycloalkyl-$(C_1-C_6)$alkyl-O—$(C_1-C_6)$alkyl, or $(C_1-C_{10})$alkyl-O—$(C_1-C_{10})$alkyl;
each $R_a$ is independently hydrogen, $(C_1-C_{10})$alkyl, $(C_3-C_8)$cycloalkyl, $(C_1-C_6)$alkyl$(C_3-C_8)$cycloalkyl, $(C_3-C_8)$cycloalkyl$(C_1-C_6)$alkyl, $(C_1-C_6)$alkyl$(C_3-C_8)$cycloalkyl$(C_1-C_6)$alkyl, aryl$(C_1-C_{10})$alkyl, or $(C_1-C_{10})$alkyl-O—$(C_1-C_{10})$alkyl;
n is an integer from 1-10; and
m is an integer from 1-10.

* * * * *

UNITED STATES PATENT AND TRADEMARK OFFICE
CERTIFICATE OF CORRECTION

| | |
|---|---|
| PATENT NO. | : 10,179,173 B2 |
| APPLICATION NO. | : 14/387178 |
| DATED | : January 15, 2019 |
| INVENTOR(S) | : Chun Wang, Wenshou Wang and John R. Ohlfest |

Page 1 of 1

It is certified that error appears in the above-identified patent and that said Letters Patent is hereby corrected as shown below:

In the Specification

Column 1, Lines 13-15, please delete "This invention was made with government support under R01CA129189 awarded by the National Institutes of Health. The government has certain rights in the invention." and insert -- This invention was made with government support under CA129189 awarded by the National Institutes of Health. The government has certain rights in the invention. This invention was made with government support under W81XWH-06-1-0677 awarded by the Department of Defense. The Government has certain rights in the invention. --;

In the Claims

Column 20, Lines 15-25, Claim 2, please delete the following compound:

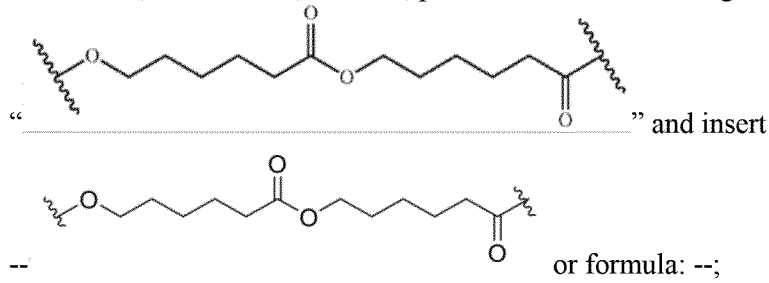 " and insert

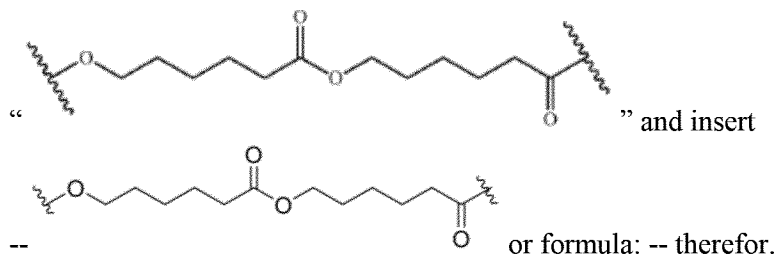 or formula: --;

Column 21, Lines 5-15, Claim 6, please delete the following:

" and insert or formula: -- therefor.

Signed and Sealed this
Seventeenth Day of September, 2019

Andrei Iancu
*Director of the United States Patent and Trademark Office*